(12) United States Patent
Bentley

(10) Patent No.: US 8,616,989 B2
(45) Date of Patent: *Dec. 31, 2013

(54) METHOD AND SYSTEM FOR ATHLETIC MOTION ANALYSIS AND INSTRUCTION

(75) Inventor: Michael D Bentley, Bedford, NH (US)

(73) Assignee: K-Motion Interactive, Inc., Scottsdale, AZ (US)

( * ) Notice: Subject to any disclaimer, the term of this patent is extended or adjusted under 35 U.S.C. 154(b) by 1041 days.

This patent is subject to a terminal disclaimer.

(21) Appl. No.: 11/834,733

(22) Filed: Aug. 7, 2007

(65) Prior Publication Data

US 2007/0270214 A1 Nov. 22, 2007

Related U.S. Application Data

(63) Continuation of application No. 11/340,088, filed on Jan. 26, 2006, now Pat. No. 7,264,554.

(60) Provisional application No. 60/647,751, filed on Jan. 26, 2005.

(51) Int. Cl.
*A63B 57/00* (2006.01)

(52) U.S. Cl.
USPC .......................................... 473/215; 473/207

(58) Field of Classification Search
USPC .......................................... 473/207, 219–221
See application file for complete search history.

(56) References Cited

U.S. PATENT DOCUMENTS

| | | | |
|---|---|---|---|
| 4,137,566 A | 1/1979 | Haas et al. | |
| 4,163,941 A | 8/1979 | Linn, Jr. | |
| 4,337,049 A | 6/1982 | Connelly | |
| 4,375,674 A | 3/1983 | Thornton | |
| 4,631,676 A | 12/1986 | Pugh | |
| 4,656,507 A | 4/1987 | Greaves et al. | |
| 4,713,686 A | 12/1987 | Ozaki et al. | |
| 4,828,500 A | 5/1989 | Seidel et al. | |
| 4,860,096 A | 8/1989 | Long et al. | |
| 5,072,294 A | 12/1991 | Engle | |
| 5,111,410 A * | 5/1992 | Nakayama et al. | 434/258 |
| 5,114,410 A | 5/1992 | Caralt Batlle | |
| 5,184,295 A | 2/1993 | Mann | |
| 5,221,088 A | 6/1993 | McTeigue et al. | |
| 5,233,544 A | 8/1993 | Kobayashi | |
| 5,342,054 A | 8/1994 | Chang et al. | |
| 5,372,365 A | 12/1994 | McTeigue et al. | |
| 5,419,562 A * | 5/1995 | Cromarty | 473/269 |
| 5,459,793 A * | 10/1995 | Naoi et al. | 382/165 |

(Continued)

OTHER PUBLICATIONS

"Swing helper built for quick learning". Dec. 10, 2004. <http://www.usatoday.com/sports/golf/pga/2004-12-10-motion-analysis_x.htm>.*

(Continued)

*Primary Examiner* — Seng H Lim
(74) *Attorney, Agent, or Firm* — Maine Cernota & Rardin

(57) ABSTRACT

A system and method for analyzing and improving the performance of a body motion of an animal or human subject requires instrumenting a subject with inertial sensors, monitoring a body motion of interest, converting sensor data into motion data and animation, comparing the motion data with existing data for motion related performance parameters, providing a real-time, information rich, animation and data display of the results in color coded displays; and based on the results prescribing a training regime with exercises selected from a library of standardized exercises using standardized tools and training aids.

18 Claims, 25 Drawing Sheets

(56) References Cited

U.S. PATENT DOCUMENTS

| | | | |
|---|---|---|---|
| 5,486,001 | A | 1/1996 | Baker |
| 5,501,463 | A | 3/1996 | Gobush et al. |
| 5,553,846 | A * | 9/1996 | Frye et al. ............... 473/455 |
| 5,575,719 | A | 11/1996 | Gobush et al. |
| 5,592,401 | A * | 1/1997 | Kramer ................... 702/153 |
| 5,697,791 | A | 12/1997 | Nashner et al. |
| 5,772,522 | A | 6/1998 | Nesbit et al. |
| 5,823,878 | A * | 10/1998 | Welch ...................... 463/43 |
| 5,826,578 | A * | 10/1998 | Curchod .................. 600/595 |
| 5,864,960 | A | 2/1999 | DeNicolo et al. |
| 5,904,484 | A * | 5/1999 | Burns ...................... 434/252 |
| 5,907,819 | A * | 5/1999 | Johnson .................. 702/152 |
| 5,930,741 | A * | 7/1999 | Kramer ................... 702/153 |
| 5,935,014 | A | 8/1999 | Lindsay |
| 5,984,810 | A | 11/1999 | Frye et al. |
| 6,041,651 | A | 3/2000 | Naruo et al. |
| 6,068,559 | A | 5/2000 | Lubell et al. |
| 6,154,771 | A | 11/2000 | Rangan et al. |
| 6,261,189 | B1 * | 7/2001 | Saville et al. ............ 473/221 |
| 6,293,802 | B1 | 9/2001 | Ahlgren |
| 6,322,455 | B1 | 11/2001 | Howey |
| 6,503,086 | B1 | 1/2003 | Golubov |
| 6,514,081 | B1 * | 2/2003 | Mengoli .................. 434/252 |
| 6,537,076 | B2 * | 3/2003 | McNitt et al. ............ 434/252 |
| 6,567,536 | B2 * | 5/2003 | McNitt et al. ............ 382/107 |
| 6,587,809 | B2 | 7/2003 | Majoe |
| 6,782,118 | B2 | 8/2004 | Verga |
| 6,793,585 | B1 | 9/2004 | Miyamoto et al. |
| 6,966,843 | B2 * | 11/2005 | Rankin et al. ............ 473/202 |
| 7,041,014 | B2 * | 5/2006 | Wright et al. ............ 473/409 |
| 7,101,287 | B1 * | 9/2006 | Wagner .................... 473/207 |
| 7,131,910 | B2 * | 11/2006 | Townsend, II ........... 473/278 |
| 7,587,065 | B2 * | 9/2009 | Matsumoto et al. ...... 382/103 |
| 7,857,708 | B2 * | 12/2010 | Ueda et al. .............. 473/257 |
| 7,887,440 | B2 * | 2/2011 | Wright et al. ............ 473/409 |
| 2002/0064764 | A1 * | 5/2002 | Fishman et al. .......... 434/252 |
| 2003/0095186 | A1 * | 5/2003 | Aman et al. .............. 348/162 |
| 2005/0085311 | A1 * | 4/2005 | Voges et al. ............. 473/221 |
| 2005/0261073 | A1 * | 11/2005 | Farrington et al. ....... 473/221 |
| 2006/0247070 | A1 * | 11/2006 | Funk et al. ............... 473/222 |
| 2007/0172797 | A1 * | 7/2007 | Hada et al. ................. 434/1 |
| 2007/0270214 | A1 * | 11/2007 | Bentley .................... 463/30 |
| 2007/0298896 | A1 * | 12/2007 | Nusbaum et al. ........ 473/131 |
| 2010/0323805 | A1 * | 12/2010 | Kamino et al. .......... 473/221 |

OTHER PUBLICATIONS

"TaylorMade Performance Lab". Nov. 18, 2005. <http://www.publinksgolfer.net/articles/154/1/bTaylorMade-Performance-Labb/Pagel.html>.*

Eckhouse, Richard H. et al, "A Comparison of Kinematic Recording Instruments", 1996, pp. 439-456, Plenum Publishing Corporation.

Lin, Andrew et al., "Application of Accelerometers in Sports Training", at least as early as Jan. 2004, pp. 1-10.

Williams, Colin, "Air-Bag Testing Requires High-Speed Image Capture", Test & Measurement World Magazine, Feb. 15, 1999, pp. 1-4, Cahners Business Information, Newton, MA.

"Midas Motion & Integrated Data Analysis System", 2000, pp. 1-2, Xcitex Inc., Cambridge, MA.

"Complaint", U.S. District Court Colorado, Case 1:06-cv-00894-WDM, *Golftec Enterprises, LLC* v *Bentley Kinetics, Inc.*, May 15, 2006, pp. 1-7.

"Answer", U.S. District Court Colorado, Case 1:06-cv-00894-WDM-BNB, *Golftec Enterprises, LLC* v *Bentley Kinetics, Inc.*, Aug. 11, 2006, pp. 1-6.

"Motion for Dismissal", U.S. District Court Colorado, Case 1:06-cv-00894-WDM-BNB, *Golftec Enterprises, LLC.* v *Bentley Kinetics, Inc.*, Sep. 1, 2006, pp. 1-3.

"Notice of Dismissal", U.S. District Court Colorado, Case 1:06-cv-00894-WDM-BNB, *Golftec Enterprises, LLC.* v *Bentley Kinetics, Inc.*, Sep. 1, 2006, pp. 1.

* cited by examiner

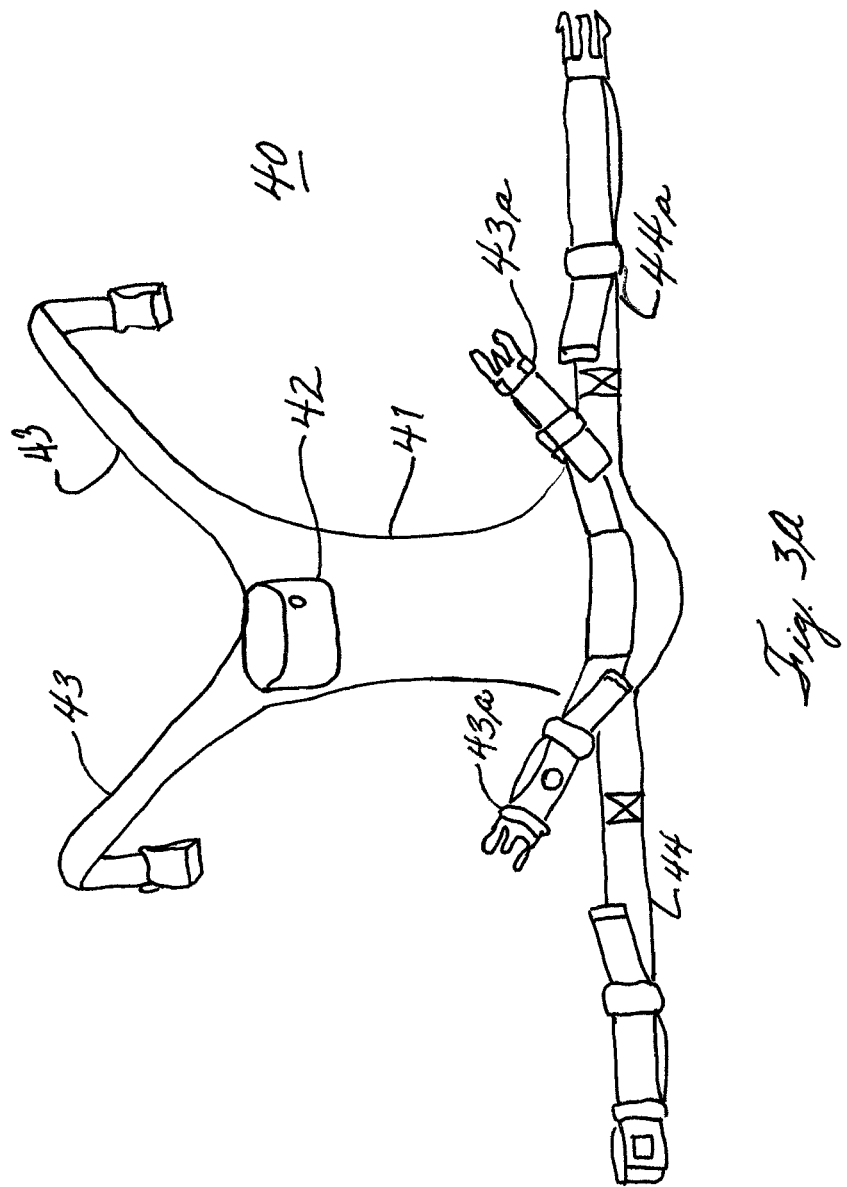

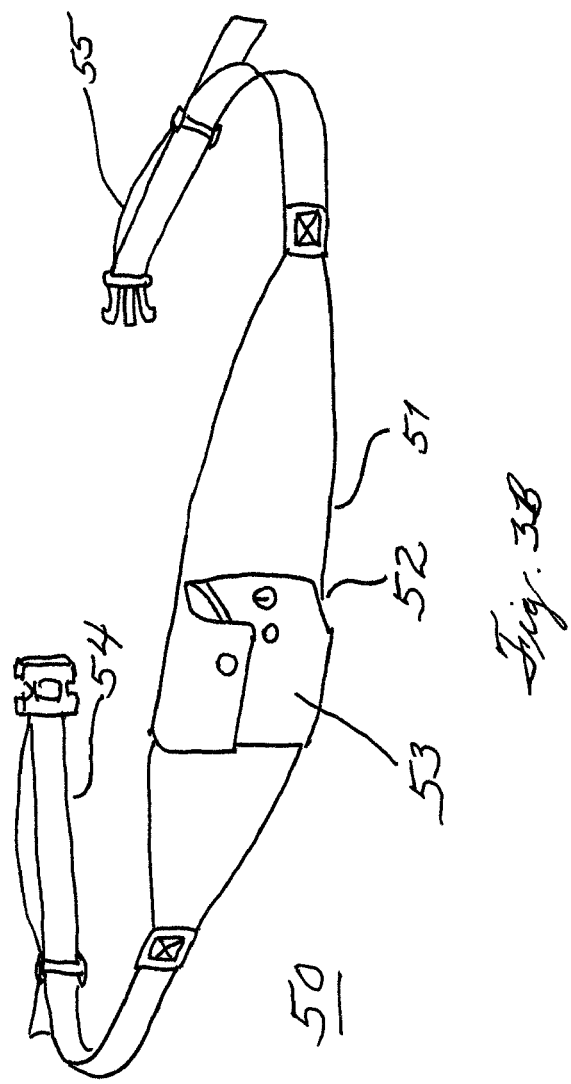

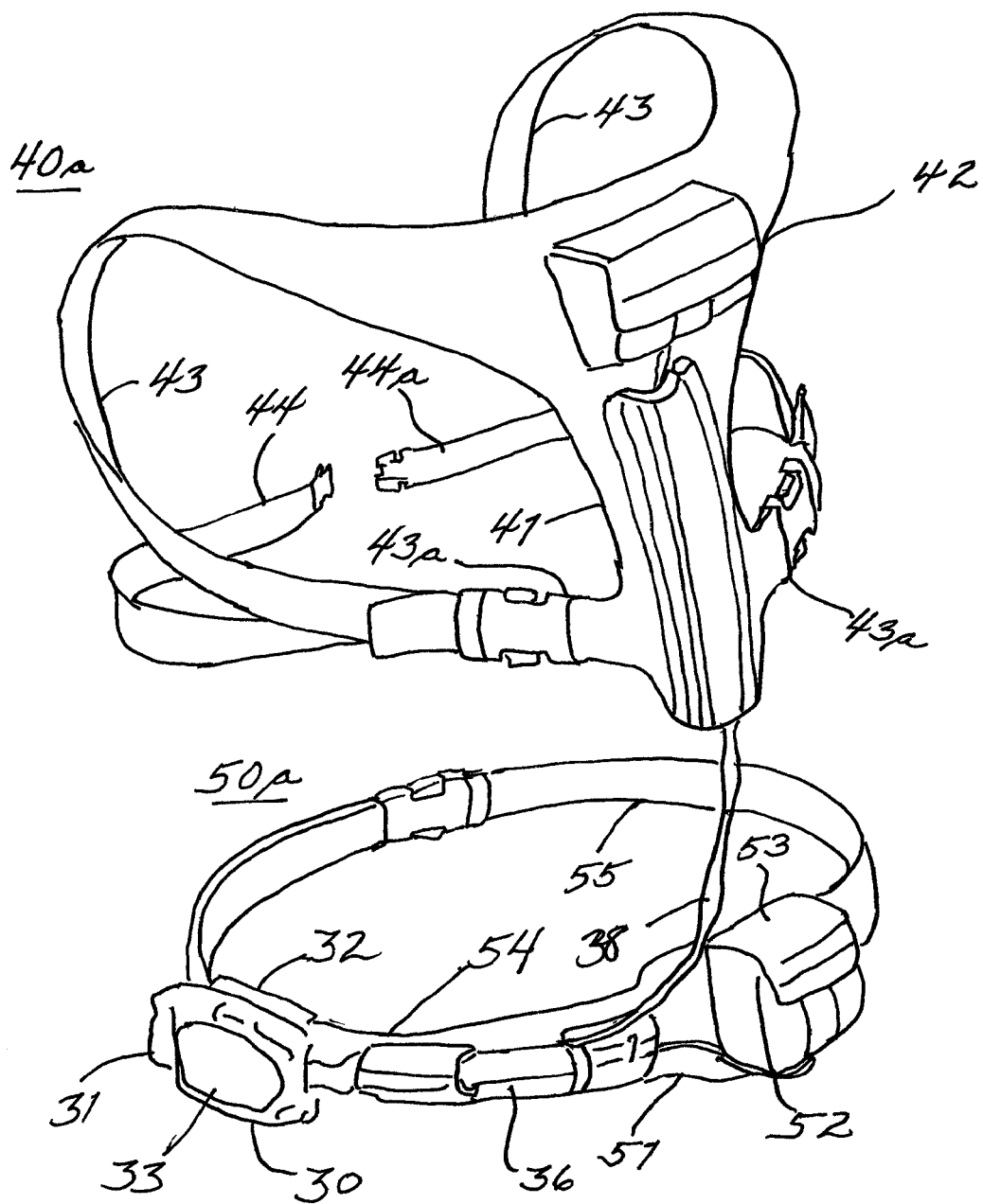

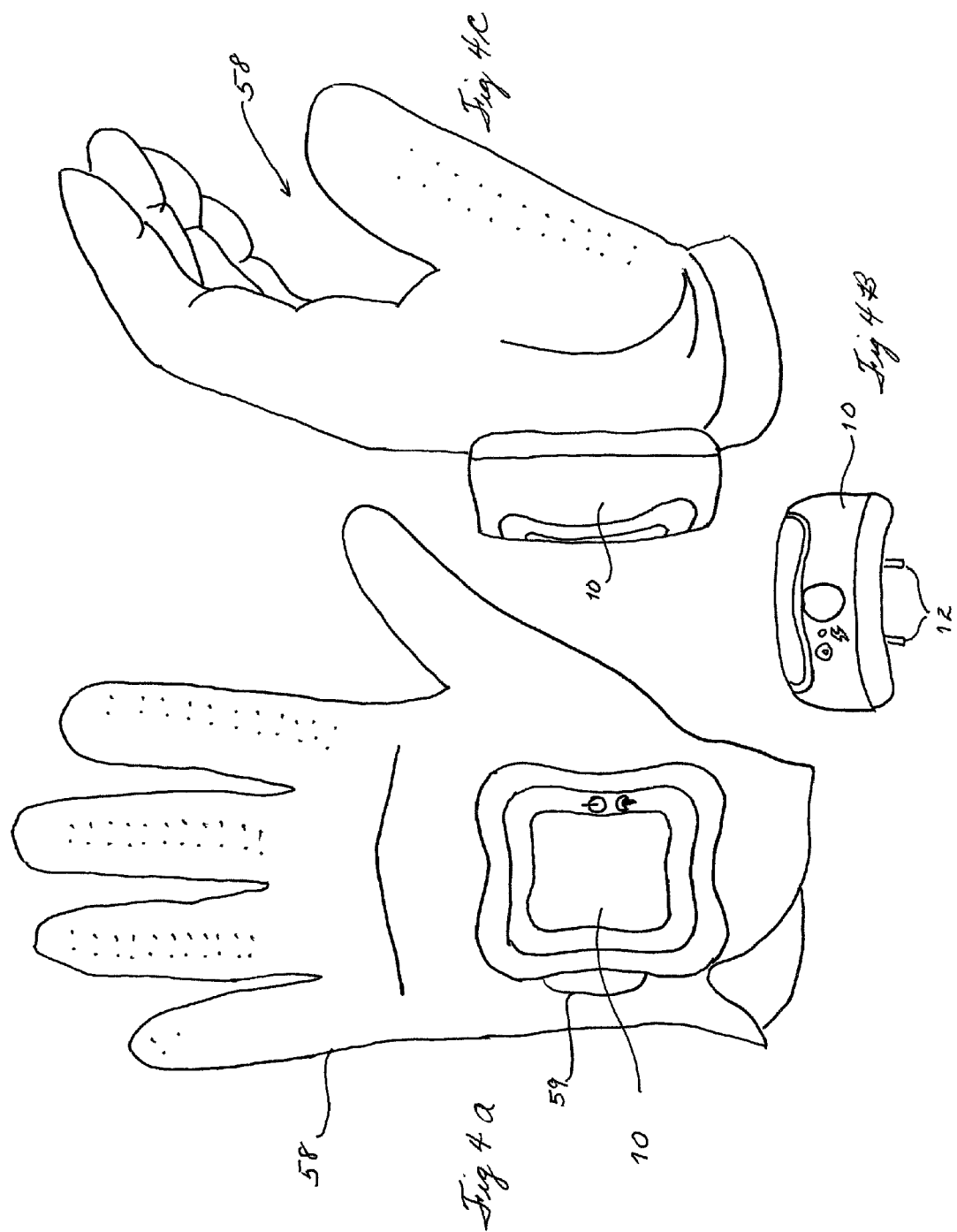

METHOD AND SYSTEM FOR ATHLETIC MOTION ANALYSIS AND INSTRUCTION

RELATED APPLICATIONS

This application is a continuation of pending U.S. application Ser. No. 11/340,088, filed Jan. 26, 2006, which claims priority to U.S. provisional application No. 60/647,751, filed Jan. 26, 2005. Each of these applications is herein incorporated in its entirety by reference.

STATEMENT OF GOVERNMENT INTEREST

This invention was made without the benefit of federally sponsored research or development.

COPYRIGHT NOTICE

A portion of this patent application, including the figures, contains material that is subject to copyright protection. Copyright notices may or may not be included in all cases. Reproduction of this material in the form published by a patent office in a jurisdiction in which this application is filed is permitted. All other rights are reserved.

BACKGROUND OF THE INVENTION

Over the course of time, many different techniques have been implemented in order to teach the proper mechanics of various athletic motions, including swinging a golf club. Many instructors, e.g., golf professionals, use a video analysis system to teach a student how to properly swing a golf club. Using a typical video analysis system, the student's golf swing is captured by a video-recording device. The instructor replays the recorded video information to illustrate the student's golf swing while providing feedback regarding the swing. Instructional feedback may be comments relative to problems associated with the student's swing, compliments regarding improvement in the student's swing, suggestions on correcting the user's swing, or any other verbal instructional comments in context with the student's swing. Visualizing one's personal golf swing in this manner has been recognized as a valuable tool in identifying problems as well as correcting those problems in order to improve the overall golf swing.

Although video analysis systems are widely used by golf professionals, these systems have drawbacks. One drawback relates to having a golf professional subjectively analyze the video information. Not only is this analysis subjective and therefore open to interpretation and subject to inaccuracies, but also such analysis is exacerbated by the fact that many problems associated with a golf swing are typically not captured by the video recording system given different camera angles, too few cameras, or loose clothing. Therefore, golf professionals are typically forced to guess the problem. Accordingly, the advice given by a golf professional may be inaccurate and inconsistent since it is difficult to isolate mechanics and measurements of the swing on video.

In order to overcome the drawbacks associated with typical video analysis systems, instructors have adopted motion or position analysis systems as an aid to analysis and instruction. Since the 1970's, universities and private research foundations have studied human motion using techniques that allow two-dimensional film or videotape to be processed into three-dimensional data. Progress had been made in characterizing the properties of human motion (biomechanics) from the simple measurements of displacement, velocity, and acceleration to the more complicated measurements of force and torque (stress). Although the scientific community has taken steps towards understanding human motion and its effects upon the musculosketal system, very little of this information has been applied to the clinical area where a patient can directly benefit.

Current motion analysis systems require that the student/athlete to wear sensor elements on their body and the sensor elements transmit positional data of isolated body parts, such as hands, hips, shoulders and head. The isolated points on the body are measured during a swing in accordance with an absolute reference system, e.g., a Cartesian coordinate system wherein the center point is a fixed point in the room. By using motion analysis, exact measurements are provided from which an instructor can more accurately determine problems in a student's swing. Even though motion analysis provides accurate positional data of the student's swing, it is not, in and of itself, particularly useful since it gives no visual aid as to where the problems may really be. When used by itself, the motion analysis system is not an effective teaching tool since the instructor is only provided with numbers and not a visualization of what the student is doing wrong. Some motion analysis systems provide animation that depicts elements of a golf swing based upon captured data. However, the animation is crude and doesn't show the golfer what he/she looks like during a swing.

Consequently, motion analysis systems are used with video analysis systems in order to try to overcome the problems associated with each system as it is used independently of the other. The instructor may use the motion capture data and subjectively map the information to the video data. Although this provides more specific data to the instructor, it is associated with at least one significant problem. The instructor, while viewing the video, must estimate the swing positions corresponding to the data points from the motion analysis information. Analysis of the swing requires not only considerable effort, but also a significant amount of estimation in associating the positional data points with an associated position on the student's swing.

Moreover, the systems for providing the video analysis are separate from the systems that provide motion capture information such that the instructor must manipulate numerous controls for displaying, to the student, the various positional measurement values as well as for providing separate video replays.

With respect to golf and the golf swing, some systems have been developed to respond to the needs of both the self-taught player and the professionally taught player. Examples of such systems are: (1) the Sportech Golf Swing Analyzer and WAVI™ system both manufactured by Sports Technology, Inc. of Essex, Conn.; (2) BioVision™ manufactured by Optimum Human Performance Centers, Inc. of Menlo Park, Calif.; (3) the Pro Grafix System manufactured by GolfTek of Lewiston, Id.; and (4) the Swing Motion Trainer manufactured by Sport Sense of Mountain View, Calif.

Other prior art teaches, for example, a system where a golfer wears a number of reflective tapes at various places on his or her body. While the player swings the club, a TV camera captures the motion of the golfer through the motion of the reflective tape. The image of the motion is digitized and the two-dimensional coordinates of the reflective tapes are calculated. The calculated coordinates are then manipulated in various ways to analyze the golfer's swing. For example, the coordinates can be used to construct a moving stick figure representing the golfer's swing.

Another system discloses a video device and method which detects the club head velocity via a colored club head and color detection unit. The club head velocity is then displayed in analog or digital form. A series of swings can then be analyzed by comparing the relative club head velocities for different club swings.

Yet another system provides a video system which displays a live video signal of a golfer's swinging motion for the golfer to see while swinging. A series of video overlays can be imposed upon the video signal for reference and analysis purposes.

There is an apparatus and method which uses a computer to produce a series of still images from a videotape of a golfer's swing. The still images are then overlaid with a series of corrected images which include lines depicting proper form. The result is then augmented with further visual or audio information and recorded onto another tape for viewing and analysis.

A golf practice apparatus provides recording and instant playback of video images of a golfer's swing. An infrared camera and flash unit are used to obtain snapshot images of the clubhead and ball just before and after impact. An optical sensor array and processor calculates statistical data on club speed, ball speed, and ball angle.

What is lacking in the field is an athletic motion analysis apparatus and method which is capable of capturing and plotting the total motion of a user with sufficient data to reduce, analyze, report on, and present the component parts of the motion and the degree of coordination of the component parts as feedback to the user in such a way as to optimize his assimilation and understanding of the information; further to provide a comparative study of the component parts of the user's performance as to its own prior test results or the performance of other persons or other benchmark values; and further, to provide a related prescription of specific exercises tailored to the user's level of performance, areas of deficiency, and available time for improving his or her skill level through practice of training exercises.

For example, as a golf swing is executed, the golfer rotates, among other things, the hips, shoulders, and arms in a sequential, and yet coordinated fashion. To maximize energy in the swing, the golfer must smoothly transfer energy from the feet to the hips, to the shoulders, to the arms, and hence to the club, culminating at the time and point of impact with the ball. What is needed is a system and method of motion capture and data processing with specialized software to process this data and generate a coordinated, multiple format presentation to the user which will effectively demonstrate the most efficient kinetic link between the golfer's motion segments, and prescribe exercises likely to improve the user's performance.

It is with respect to these and other considerations that the present invention has been made.

SUMMARY OF THE INVENTIONS

A kinetic link in the context of the invention is a chain of interdependent components of motion acting towards a common goal, the effective and efficient execution of the motion. This kinetic link principle is applicable to all dynamic, athletic-type body motions intended to perform work or convert or transfer energy in any manner by means of bodily exertion, with or without the use of a hand or foot actuated or operated tool or article of sporting equipment. For example, in a golf swing motion, the process of striking a golf ball with a golf club, the kinetic link is composed of four principle components of the motion with three links. These four components and three links in combination represent the full motion of the body. The components consist of the hip segment, shoulder segment, arm segment and the club. The links include the musculature found between each body segment. Since the frame of reference and the point from which this type of motion must be leveraged is the ground itself, a complete analysis of the motion must consider the feet first, then overall posture, then hips, then shoulders, then arms, then club, and finally the ball. A weakness at any point in the kinetic link results in a less than optimal total performance. Means of identifying and improving the component parts of the motion will improve the overall performance. This assumption is at the foundation of the present invention.

The invention, in the broadest sense, may be a global, knowledge-based, enterprise system and method for providing performance testing and training regimes to persons for whom athletic activities such as golfing and others for whom repetitive athletic motions are an inherent part of their normal work or recreational activities, for improving the effectiveness of their golf swing or other specific athletic motion.

A typical example of the system and method uses state of the art technology and equipment for instrumenting a user or subject and monitoring a motion, draws upon and contributes to a vast library of performance data for analysis of the test results, provides an information rich, graphic display of the results in multiple, synchronized formats for user viewing and/or monitoring by a coach or system operator, and based on the results prescribes a user-specific training regime with exercises selected from a library of standardized exercises using standardized tools and training aids.

Users and their coaches may access the library of performance data to see and compare a user's most recent test performance to its own or other testees' prior test results. After an appropriate amount of off-line exercising, and/or at the desire of the user or coach, the testing is repeated. The specifics of the prescribed training are re-calculated and may include a weighted consideration of the current performance testing result in addition to prior test results. The performance reports provide an objective record of the type and degree of changes in performance that the user has experienced.

The system may be employed during live practice sessions to provide essentially instant or "real time" visual and/or auditory biofeedback, or provide "replay" presentations, of each successive attempt at a particular drill or a full motion. Deviations in specific parameters from the objectives of the prescribed drills are reported and the user has the immediate opportunity to respond to the feedback and reduce the deviation of the specific parameter during an immediate next attempt at the same drill.

In one embodiment, the invention is a local system or method for golf swing motion analysis of a golfer, intended to improve the golfer's performance by repetitive use. The invention includes the use of multiple body and/or tool mounted sensors, wired or wireless transmission of sensor data in real time to a receiver/computer and database system for data processing and analysis, along with a video and/or audio recording input of the test. Results are instantly generated by the system, consisting of associated forms of biofeedback including graphical representations of coordinated and comparative data output on components of the full motion, along with animations of the motion generated from the motion data, and actual video of the motion. The three forms of feedback are combined in their presentation for ready assimilation and understanding by the golfer and/or instructor in either an immediate form to enable sequential, monitored attempts with intermediate feedback, or a later feedback mode with an extended period for practice of prescribed drills intended to improve aspects of the motion.

The analysis reduces the full motion to predetermined major component motions. The coordinated data output portion of the results may represent the relative timing and amplitude of components of the user's own motion. The comparative data output may represent a comparison of the relative timing and amplitude of components of the user's motion to the same components of an expert or other standard performance data from the system database, or the user's own prior test performance data. The data processing and biofeedback may further include prescriptions from a database of standard exercises, tailored according to the user's level of performance and time available, for training on a component-of-motion basis, such as stance, balance, hip motion, and shoulder and arm motion, adjusted according to the user's actual performance data. The exercises may prescribe or presume the use of specialized tools and training aids from among a library of pre-determined tools and training aids, during the exercises.

As described above, the data input, analysis, and the biofeedback report is preferably augmented by use of video, audio, and other recording devices emplaced and focused to capture additional motion data at a desired direction from the user under test, and processed to provide additional graphical, video, audio or other form of output that can be integrated with the data output for optimal user understanding and assimilation of the analysis and report.

The system and method in local or global embodiments may be applied to other athletic or occupational motions by which energy is transformed through user motion into work of any type, for improving performance, preventing injury and/or providing a rehabilitation program.

A set of inertial motion sensors are attachable to the user's body, and/or motion tool or device such as a golf club, at strategic points by the use of specially designed appliances. Each motion sensor contains a multi-element sensing system and circuitry for sensing and reporting three dimensional position and attitude of the sensor, transmitting a real time output of vector data for further application-specific processing. One embodiment of the multi-element sensing system within the motion sensor includes three gyroscopic inertial sensors, three accelerometers, and three magnetometers, as is produced by InterSense Inc., of Bedford, Mass. Motion data is typically updated at a rate of 120 Hertz from a system employing three motion sensors, although systems with fewer and more motion sensors and with faster and slower position update rates are within the scope of the invention.

The vector data from the full set of motion sensors is sufficient data from which to derive and characterize the principle components of a golf swing or other athletic motion, as is further described below. The information is transmitted in near real time directly from each sensor individually, or via a common transmitter to which some or all the sensors may be hard wired, to a nearby receiver and hence to a processing computer for application-specific data processing and analysis, and generation of data and graphical output reports representing the user's performance, as is further described below.

The processing computer can perform relational calculations on the data received from the various sensors, thereby allowing computation of various application-related parameters of interest. As an example, the processing computer with its golf-specific software can calculate club-face angle or the angle through which the golfer turns his or her shoulders while swinging the golf club. Such parameters are referred to here as "performance parameters."

In a golf swing motion analysis system in particular, inertial sensor data is typically processed into the following parameters relating to the golfer's body performance: hip velocity (degrees per second); hip rotation (degrees negative and positive); shoulder velocity (degrees per second); shoulder rotation (degrees negative and positive); club release (degrees per second); club speed (miles per hour); club face rotation (degrees open/closed); club path (degrees inside or outside of club's address position); hip linear movement (centimeters left or right of neutral address); hip shoulder separation (time difference between maximum hip, shoulder, and club velocity); flexion/extension of hip segment (centimeters traveled along z-axis); and kinetic link. These parameters are further extrapolated to yield a predicted "ball in flight" resulting performance of parameters: spin (degrees per second); launch angle (degrees); carry distance; roll distance (yards); total distance (yards); distance traveled off line (yards right or left); ball flight character (fade, draw, hook, slice, push, pull, straight); and PTI or power transfer index.

The processing computer can also display information about the swing that will allow the golfer or his instructor to visualize and adjust the swing. For example, in one aspect, the system displays live video feed of the golfer (obtained through a video feed from a video camera critically positioned adjacent to the golfer and coupled wirelessly or otherwise to the processing computer), an animated simplification of the same motion generated from motion data, and statistics reporting the state of the various parameters in any given freeze-frame. The system can also display the results of the various calculations of performance parameters, as described in the previous paragraph, which characterize the swing over time; for example, the system can display data regarding the club-face angle or the angle through which the shoulders rotate during a particular swing.

A system interface between the processing computer and the golfer in the form of a control or feedback module mounted on or near the instrumented golfer can provide instructions to the golfer in preparation for or in response to a particular attempted golf swing. The system interface may instruct the golfer, for example, to address the ball, give a five-second window for the golfer to initiate a swing, etc. Such instructions may in one embodiment be in the form of audible beeps, or synthetic speech or pre-recorded voice commands. Colored lamps or a backlit LCD or other type visual signal display can also issue coded or alphanumeric instructions. Such functions are useful in securing specific and timely inputs needed to calibrate the sensors for absolute position, as well as to coordinate the orderly sequencing or progress of a testing session.

In one response mode, the system can be characterized as operating in a "biofeedback mode," where the processing computer through the system interface assists the golfer in following prescribed exercises (described in more detail below). In that mode, the processing computer can also display on its display unit or screen, to the golfer and/or his instructor, one or more calculated performance parameters and video images of the golfer. Calculated diagnostic parameters of interest can be reported on the screen, stored for later analysis, or converted into success or failure codes, which can be transmitted back to the golfer and/or his instructor, or any combination of those actions.

Codes transmitted as biofeedback to the golfer may be in the form of a tone or a color that differs between a successful swing and an unsuccessful swing. For example, if the system is programmed and set up for training the golfer in a set of exercises where the golfer tries to rotate the shoulders through exactly 40 degrees from vertical, the system, as through a control module, can alert the golfer through tones or lights or changing colors within the graphic display screen when the swing differs from the ideal rotation angle by more than a predetermined error. For example, only if the rotation angle falls between 35-45 degrees, will the swing be considered a success. The tones or changing lights may have several bands or ranges, allowing intermediate or scaled results. For example, a red light might follow a swing in which a diagnostic parameter badly diverged from ideal, a yellow light might follow a swing in which the same diagnostic parameter only somewhat diverged from ideal, and a green light might follow a swing in which the same diagnostic parameter diverged from ideal by less than the pre-assigned margin of error. The signal light may be the background color of an animation. The information conveyed by the changing color of the selected illuminated portion of a screen may be likewise presented with same or more or less detail in other audio, textual, numerical and/or graphical formats, including numbers, bar graphs, line graphs and text messages. Oral callouts may be used in combination or in the alternative.

The feedback report may also be continuous or highly differentiated; for example, the length of an audible tone might correspond to the extent to which the diagnostic parameter diverged from ideal, and the golfer is instructed to practice until the tone shortens or disappears. The number of blinks of a light, light color, sound frequency, sound volume, tone length, and tone type are among the characteristics that can be used in the feedback mode. The audio format feedback information can be produced with synthesized voice output from a speaker or earphones.

The processing computer and system interface also can include monitoring by a golf professional or other motion expert or instructor, directly or remotely as through an internet connection, and allow him or her to transmit to the golfer instructions to initiate, cease, or control exercises through instructor command inputs to the system, or received by the system from a remote location, such as through an internet connection.

After computation of the various golf-related parameters of interest, those diagnostic parameters can be utilized by indexing a cross reference table of test results and exercises to automatically prescribe to the golfer an assignment of appropriate individualized exercises to improve his or her swing. In a one embodiment, each calculated diagnostic parameter is divided into two, three, or more ranges, with each range corresponding to a prescribed action with respect to a particular exercise. For example, a first range for a particular diagnostic parameter can result in a prescription of a certain exercise, a second range of the same parameter can result in a different prescription, and a third range of the same parameter can result in no prescribed exercise because the golfer does not have a problem with the particular aspect of the swing that the parameter measures. The different prescription in each example can be, for example, a specific different number of repetitions of a given exercise, a different priority level given to a given exercise (see next paragraph for priority levels), a different exercise tool or accessory being used for a given exercise, or an entirely different exercise. Further, the frequency and duration of the exercises may be apportioned by the prescription compiler in accordance with the golfer's available time and schedule, as it was previously inputted to the system by the golfer.

Alternatively, the prescriptions may result from combinations of results from two or more diagnostic parameters. In variations, the knowledge base may include rules developed through expert interviews, automated analysis techniques based on measured results produced by the swing, or principles of fuzzy logic. In one embodiment, the diagnostic parameters produce exercise prescriptions with assigned priority levels. For example, if a particular golfer's swing produces one diagnostic parameter that is very far from ideal while other diagnostic parameters diverge from ideal only partly, the first diagnostic parameter will be assigned a higher priority level than the others. For another example, if two diagnostic parameters diverge from ideal but one is considered more important to a good golf swing or alternatively one is considered important to control to provide a good foundation for the other, then that one will be assigned a higher priority level than the other.

In one embodiment, each prescribed training exercise is assigned a priority level from one to nine, and several exercises may be assigned a common priority level. In that embodiment, the golfer or the instructor can indicate by input to the computer how much time the golfer has available to perform the exercises, and based on that information, the system can recommend which ones to perform. For example, if an athletic motion analysis system projects a need for three exercises with a priority level of one, five exercises given priority level two, and four other exercises with higher priorities, and if each exercise has been determined to require at least fifteen minutes to perform for reasonable effectiveness, and the golfer has a limited time for exercise, then the system might assign or prescribe accordingly. As specific examples, if the golfer indicates that he has one hour available, the assignment may be performing only the three priority one exercises for twenty minutes each. If the golfer has two hours available, the system might prescribe performing all priority one and all priority two exercises for fifteen minutes each. If the golfer has three hours available, the system might assign all exercises for fifteen minutes each. The minimum times to perform each different exercise might vary, the time recommended to perform any particular exercise might vary or be fixed, and the gradations of priority can be changed as desired.

The diagnostic parameters can also or alternatively be used to prescribe, select or fit golf equipment to the golfer, such as golf clubs or golf shoes from among one of several types or customized versions having particular measured parameters. For example, the length, lie angle, loft, or weight of a particular type of golf club can be selected based on analysis of the diagnostic parameters calculated for the golfer, preferably in combination with parameters about the golfer, such as his or her height, hand length, and foot size.

In another aspect, parameters calculated at time of impact, such as position and orientation of the club face relative to the ball and velocity vector and face angle of the club, can be used to predict the forces on the ball and thus predict its trajectory. Knowledge of the terrain can allow determination of the distance and path of the struck golf ball, or alternatively the calculation can predict distance assuming the terrain is flat. Such predictions based purely on force calculations can be supplemented with information about the behavior of the ball in atmosphere, such as through testing of particular types of golf balls, to adjust for air resistance. In a further variation, wind direction and velocity can be taken into account, with such data input into the system manually or through an electronic anemometer or local air data station coupled to the system electrically, or via an internet or wireless connection.

The system may be remotely or locally controlled so that an off-site or on-site instructor may direct the operation of the system or monitor the results. In a purely user-contained mode, control inputs for set up and testing operations may be entered, test exercises performed, and swing data viewed and reviewed by a user with the aid of a personal control module and data monitoring system such as a belt-worn control/display unit or module.

The methodology and the system are applicable to other repetitive athletic and occupational motions for testing of animals or humans, analysis, reporting, diagnostic review by coaches, trainers and/or medical personnel or physical therapists, with prescriptions being similarly generated for training to improve performance, prevent injury, or for rehabilitation of various motion capabilities where the motion is susceptible of data collection and reduction into component parts in the manner described above, and the report can be presented in a synchronized, composite display of animation, multiple data tracks and video format.

It is an additional goal that the report and the prescribed regime of practice drills can be taken home as a recording in any useful format, or accessed from home through a browser-based, on-line access point connecting to the local system or to a host, knowledge-based enterprise system to which it is connected, for later review and practice.

Therefore, the invention in one aspect consists of a method and apparatus for analysis and improvement of a selected athletic motion of an individual, consisting the steps of using a computer-based motion analysis system that has a processing computer, inertial sensors, a video camera which may be of any analog or digital technology, and a computer-driven display screen; testing an individual doing the athletic motion, with a tool if a tool is implied, by monitoring the execution of the motion with multiple inertial sensors mounted on the individual and optionally on the tool, with the video camera or cameras directed at the individual in action. The athletic motion might be golf, baseball, hammering, sawing, throwing or using other handheld tools or sports equipment, a small sampling of which may include balls, bats, rackets, clubs, paddles, oars, spears, hammers, screwdrivers, staple guns, darts, horseshoes, and axes and others. It extends to running, kicking, jumping, pedaling and other foot/leg athletic motions using foot actuated tools and sports equipment including bicycles, balls, and foot-operated levers and other tools and objects.

The video camera, when used, is carefully positioned in advance to insure precise alignment with the individual under test and useful points of reference for measurement and analysis of the motion. The sensors are carefully positioned with the use of body wearable appliances to insure that sensor data will reflect body motion accurately. Sensor data is collected from the sensors and video signal from the camera during the execution of the athletic motion; and the sensor data is analyzed by processing the sensor data into motion data representing pre-defined selected performance parameters of pre-defined selected components of the athletic motion as may be accomplished by or attributable to specific or distinctive body segments such as the leg, hip, shoulder, neck, head, arm and hand aspects of a motion. The results of the analyzing is reported or presented in a form that includes a real time, computer generated display of multiple, selectable configurations, one of which includes in a composite, synchronized combination of the video signal as a video display, a multi-color, three dimensional animation representing the motion of at least one color-coded body segment created from the motion data, and a time-based graph of multiple selected performance parameters.

There may be provision for setting a range of motion limit for selected components of motion such as a specific bending or flexing component of the motion in advance of the testing. The animation of the motion may incorporate a three dimensional wire mesh cage or open frame representing the motion limits within which the body segment is visible. The software may provide for altering a selected color within the display upon the occurrence of a motion exceeding the motion limits, as a highly visible, instant signal to the individual that the limit has been reached or exceeded. Stepped levels of indication of approaching or exceeding pre-set limits may be used by using multiple color changes such as from green to orange to red.

The analysis may include for selected parameters comparing the motion data test value to a pre-defined benchmark value for the same parameter and determining a degree of deviation, and presenting on a time-based graph the test value and the benchmark value concurrently. The analysis may include calculating from the test values and the benchmark values a score for each selected parameter. It may further include combining the scores of the selected parameters by a pre-defined formula so as to yield a single score representing the total performance value of the athletic motion as a kinetic index.

The system and software may include with or follow the report or presentation with a prescription of a regime of training exercises selected from a pre-defined list of exercises based on the amount of the deviation from the benchmark values of individual parameters, and the exercises may be associated with a pre-defined list of training tools. The frequency and length of periods of exercise may be limited by the available training time of the individual, as may have been entered into the processing computer ahead of the testing.

The wireless inertial sensors may employ a stacked topology within a sensor enclosure wherein a battery is proximate to and its shape conforms to the bottom of the enclosure, and sensor elements and electronic circuitry are positioned over the battery within the enclosure. The sensors may be attached to body appliances that are worn by the individual. The sensors and the appliances may have correspondingly keyed mating structural by which the sensors are uniformly and repeatably attachable to the same place with the same orientation on the appliances.

The results of the analyzing, including the motion data and the video data, may be stored in a local or remote computer database and made available for later replay locally or via a remote computer or computer network connected or connectible to the processing computer.

The camera may be set up in advance of testing using a reference target or frame placed on the test site so as to define at least one point or line of reference relative to the motion to be tested. The software may be configured for overlaying the video display during a calibration phase with reference points, lines or other symbols relating to aspects of the motion, such as alignment lines, center lines, balance points of the starting, ending or in-motion positions of the testee, by which motion can be more critically observed. The effectiveness of the lines and symbols overlaid on the video display may be dependent on correct camera placement prior to testing.

Other and various aspects, goals and objectives of the invention will be apparent from the examples and illustrations that follow. Pronouns should be interpreted in all cases to include both genders.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is a diagrammatic backside elevation view of a vest appliance of the invention, illustrating the location of a sensor pocket high on the back panel.

FIG. 3B is a diagrammatic perspective view of a waist belt appliance of the invention, illustrating the location of a sensor pocket on the back panel.

FIG. 3C is a diagrammatic perspective view of a vest appliance and a waist belt appliance configured with sensors in sensor pockets hard wired to a control module on the waist belt appliance, from which wireless transmissions of sensor data emanate.

FIG. 4A is a top view of one sensor embodiment, mounted on a glove appliance.

FIG. 4B is a bottom edge view of the sensor of FIG. 4A, illustrating the attachment loops protruding from the curved underside of the sensor case, by which the sensor is attached to the glove appliance.

FIG. 4C is a side edge view of the sensor and glove appliance of FIG. 4A.

DETAILED DESCRIPTIONS

An athletic motion analysis system and method for improving performance according to various aspects of the present invention consists of equipment and methods, including cameras, inertial sensors, computers, computer networks, and software, means for providing real time visual feedback in unique formats and prescriptions for practice exercises, all as described in the following paragraphs. The invention comprises many embodiments and variations of which the following examples are illustrative and not limiting.

Figure 1:
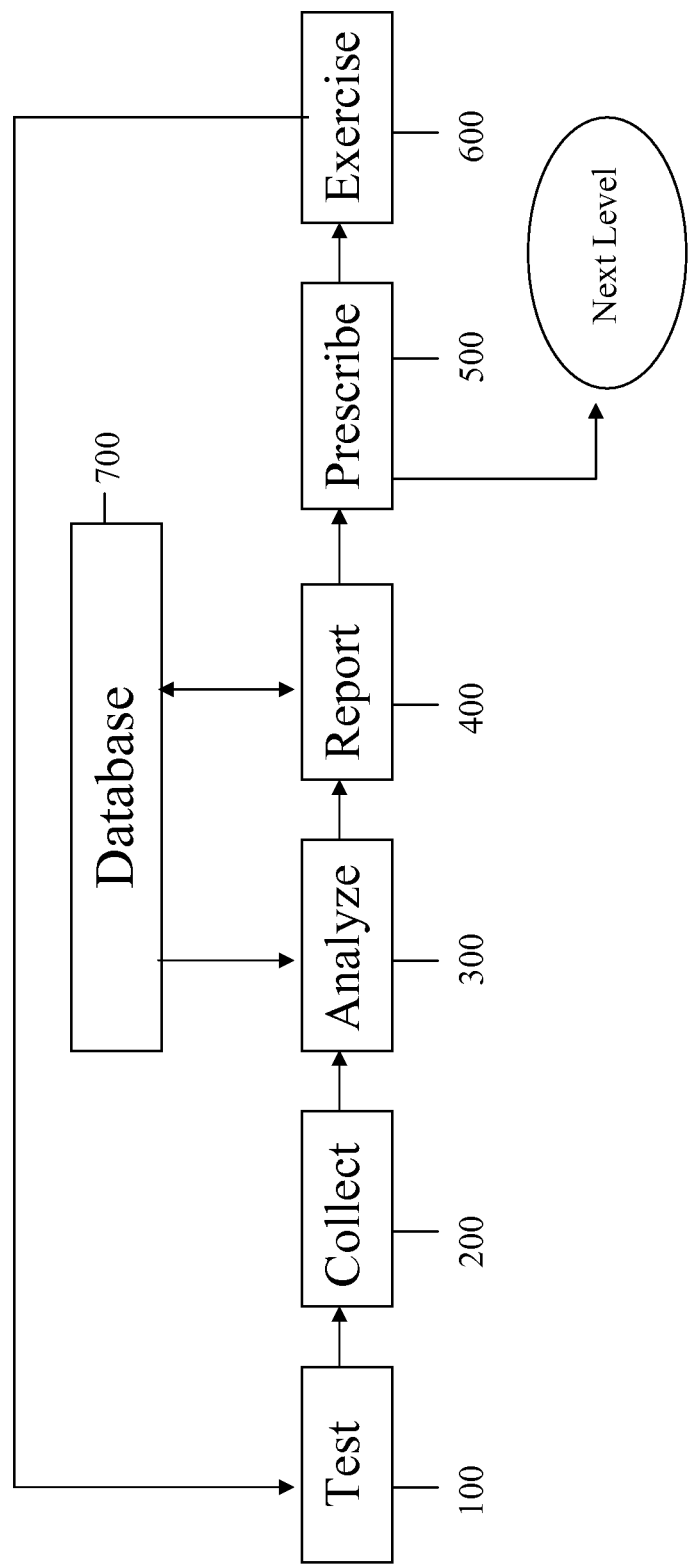
FIG. 1 is a simplified flow chart depicting the basic, repetitive, step-level methodology of the invention in which improvements in sequential performance testing are considered in the prescribing of the next sequential set of exercises.

Referring to FIG. 1, the steps of one embodiment of the invention are presented in sequence. Test 100 requires that the user subject him or herself to testing by use of the system of the invention while he/she conducts an athletic motion of interest. Collect 200 includes the measurement and collection of motion data with inertial sensors, a camera, and possibly other sensors, of the motion executed during the test. Analyze 300 includes analyzing the collected data, and includes accessing a database 700 of related data for comparison and for relating types and degrees of deviations in performance from benchmark values to a library of standard exercises for generating prescriptions of appropriate practice exercises or corrective measures. Report 400 includes the generation of a unique display of synchronized video, motion animation and data/time graphs. Prescribe 500 includes the documentation and delivery of a program or regime of type and time or quantity of performance parameter-specific exercises.

Finally, exercise 600, instructs the user to practice the exercises or corrective measures in accordance with the prescription. The cycle of test, collection, analysis, report, prescription and exercise is repeated as often as desired until the desired level of performance is achieved. The type, time and level of the prescribed exercises are adjusted automatically (up or down) according to the most recent performance and/or the change in performance between the most recent performance test and prior reported test results.

Figure 2:
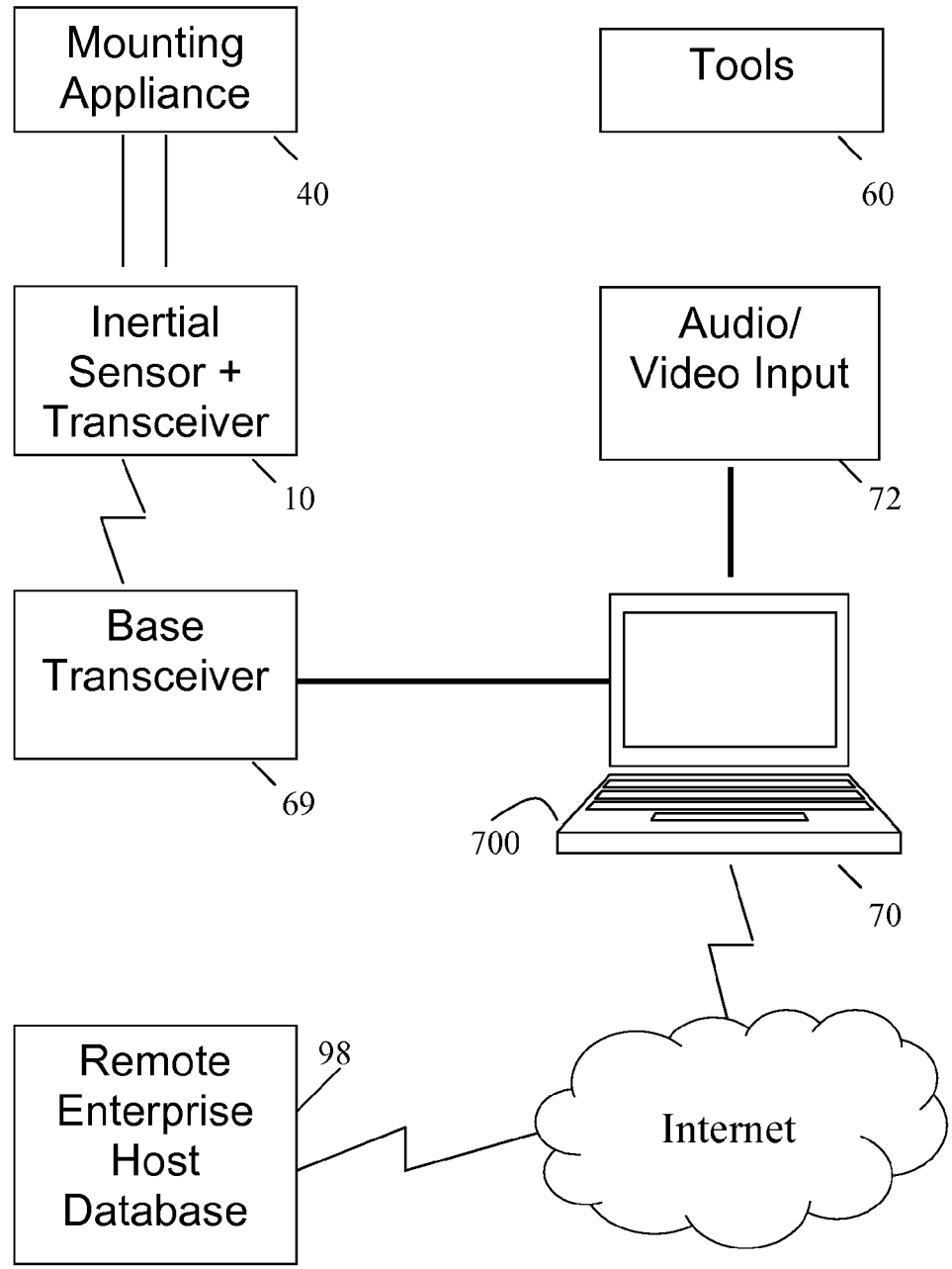
FIG. 2 is a diagrammatic illustration of the principle components of an embodiment of the invention, including the inertial sensor/transceiver, audio/video sensors, base transceiver, and computer with its control/display unit, and internet connection to a enterprise host and database.

Referring to FIG. 2, the principle components of one embodiment of the system and their relationship is represented in a system diagram where inertial sensors 10, attached to body appliances 40 that are worn by the user, communicate by wireless means with a base transceiver 69 which is part of a computer-based motion analysis system 70 that includes a control and display capability, such as a laptop computer, with suitable application software and an onboard or connected database 700. Other sensory devices 72, at least one video camera and optionally a microphone and other sensors, are connected to system 70 by wire or wireless means. System 70 processes motion data and generates, displays and/or transmits reports and prescriptions as described in more detail below. Training tools 60 are not directly linked to motion analysis system 70 or the other associated components, but may be used by the user or testee during practice exercises as prescribed by the system after testing and analysis, all as is further explained below.

System 70 and its related components may be operated at times on a stand-alone basis, but may always or at times be connected or connectable to a remote, knowledge-based enterprise system and database 98 via a browser-based internet access point or other high speed data connection for conducting data transfer and enterprise related activities between the host and local systems.

For example, a website for the enterprise system and host database 98 may provide access for registered user systems 70 to the host company's information, motion analysis products and services information, management information, company news, user access via a log-in screen for product and service FAQs, news letters, and database 700 libraries of past performance and benchmark data and exercises, and updates thereof.

The website may be configured to provide such global functionalities to registered users as general prescriptions and exercise instructions, explanations, and illustrations—text and/or audio/video, clubhouse events and news, discussion forums, special links for members, global FAQs, an on-line store link, special newsletters, and access to relevant documents and training tips. The website may be divided by categories of registered users pages as between student users and instructor users and provide such particular functionalities as either group might need, such as for instructors the history of instruction sessions by student portfolio, the history of student analysis by portfolio, with sessions organized or stored in respective student "locker rooms" by portfolio, and scheduling for student sessions. Student pages may provide such functionalities as the individual's own personal data, history of his sessions and analysis, his training calendar, instructor contact info, and his golf scores and stats logbook.

There may be a third class of user, an organization user such as a golf school or academy, where a subset of the enterprise system is treated as an OEM client or model, with its own branding, hosting multiple students and instructors as described above.

Individual systems of the invention work in stand-alone configurations as individual test and evaluation systems for collecting student performance data, analyzing and comparing student data to a library of performance data including expert performance data, reporting the results, and prescribing corrective exercises. New test results are added to the database, and may be delivered to or accessed by coaches and/or students via on-line access to internet services. Individual systems may share access to a host database of test results of other users and related practice drills for study or comparative purposes.

Alternate embodiments of the invention may be directed to other athletic, occupational, or rehabilitation motion analysis and training of animals or humans, at either an enterprise level or a local system level as described below.

Referring to FIGS. 3A, 3B, 3C, 4A, and 4C, various embodiments of body appliances for attaching motion sensors to the user's body and/or golf club are illustrated. The appliances are designed to be repeatably donned by the user such that the sensor assemblies are positioned and repeatedly repositioned in the same place on the body or club for optimal motion sensing at selected critical points of anatomy, particularly skeletal anatomy and/or tool structure, where they will provide motion data sufficient to define the initial position and full range of motion such that it can be reduced by data processing to the major component motions. The appliances are further refined structurally to minimize or avoid interference with body motion during execution of the movement under study. The appliances are yet further refined to retain body or tool position and to retain the relationship of the sensor assembly to the target area of the body or tool during normal body motion, including any strenuous flexing and/or acceleration associated with the motion under study, so that the change of position data reported by each sensor most accurately reflects the real time experience of the target area of the body and/or tool.

In one example, for a golf swing analysis system, there are a series of three appliances for mounting inertial sensors to the user's body. There is a vest appliance 40 (FIG. 3A) suitable for mounting an inertial sensor, referred to as a shoulder sensor, high on the user's back above and between the shoulder blades over the spinal column; a waist belt appliance 50 (FIG. 3B) for mounting an inertial sensor, referred to as a hip sensor, low on the user's back just above the hips and over the spinal column; and a glove appliance 58 (FIGS. 4A and 4C) for mounting an inertial sensor to the back side of the user's forehand.

Figure 4D:
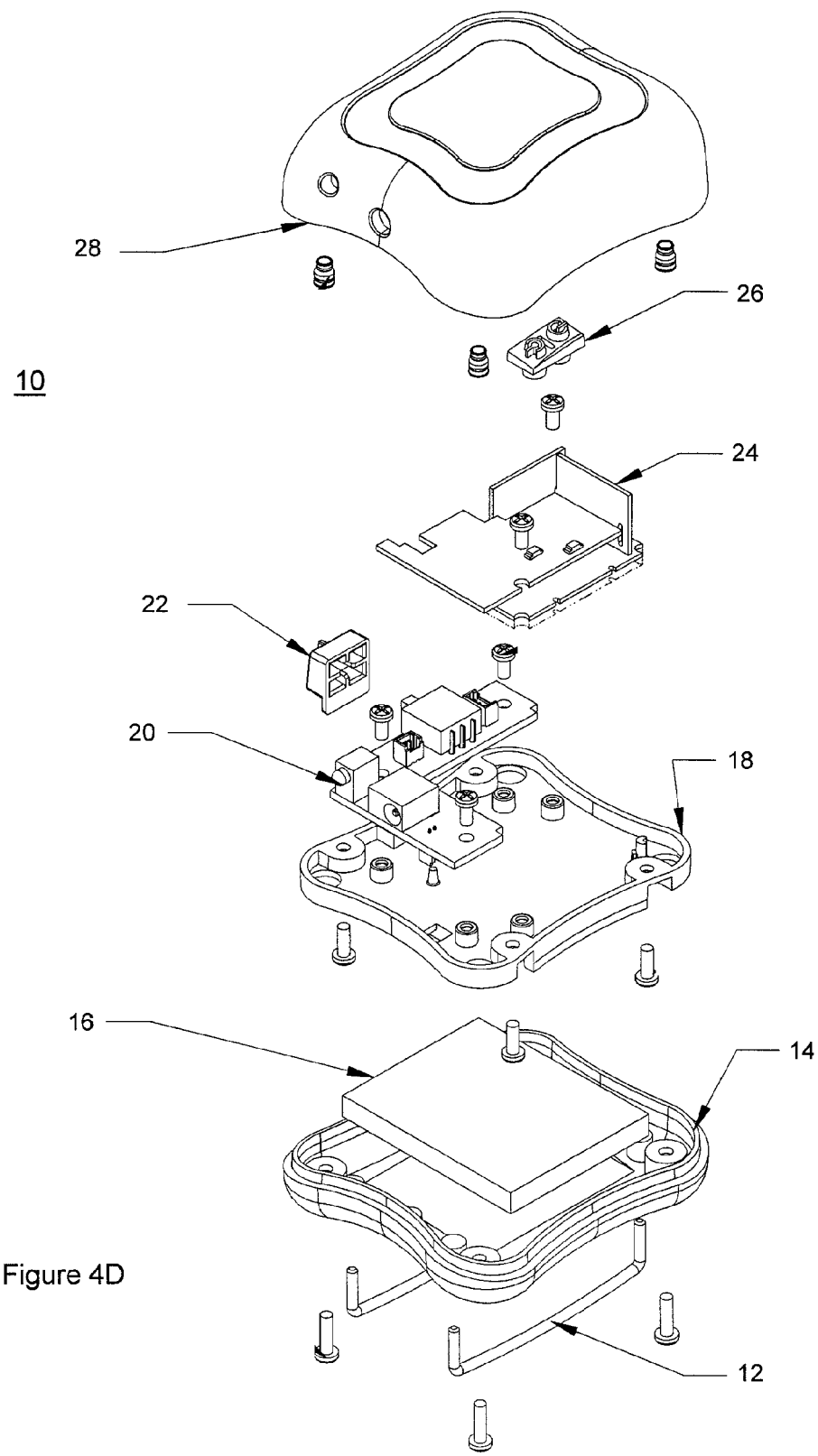
FIG. 4D is an exploded perspective view of the sensor of FIG. 4A, illustrating the stacked arrangement of electronic components over the curved battery, and the attachment loops protruding from the underside.
Figure 5:
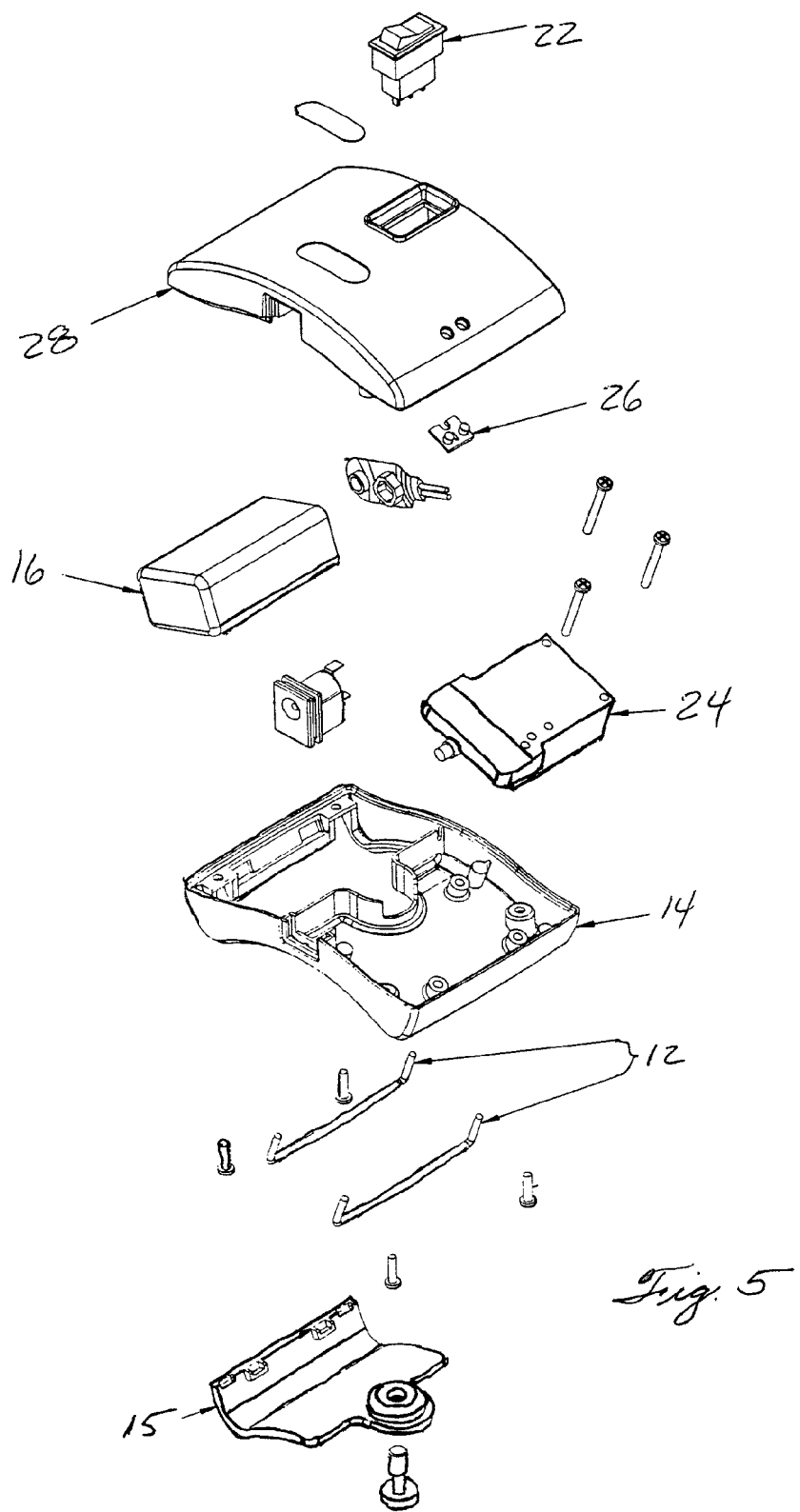
FIG. 5 is an exploded perspective view of another sensor embodiment, that may be wired to a control module-transmitter for transmission of sensor data.

Referring to FIGS. 3A and 3C, vest appliances 40 and 40A respectively have a back panel 41 at the top of which is attached a sensor pocket 42 suitable for snuggly securing a respective sensor 10 or 10A. Not visible in the figures but easily understood, the back side of the pocket that will receive the underside of the sensors of FIGS. 4B, 4D, and 5, is slotted to accept mounting loops 12 in a keying manner that enhances the grip and position integrity of the sensor within the pocket of the appliance.

The slots or sockets for receiving the sensor loops may be characterized as mounting structure, and may be further configured with latch mechanisms that secure the sensor loops 12 within the receiving slots or sockets of the sensor pocket with a mechanical interlock. Variations of the sensor loop structure as a mounting clip or stud and of the pocket slot as a keyed receiver structure, with a latching mechanism such as twist or click fit mechanism incorporated on either or both the appliance and the sensor are within the scope of the invention. The sensor pocket may be reduced in this instance to a mere location on the appliance rather than a full or partial enclosure for the sensor.

Shoulder straps 43 extending from the top corners of back panel 41 attach to strap ends 43A extending from the lower corners of the back panel via buckles. Chest belt sections 44 and 44a extend from the lower corners of the back panel for buckling on the front side of the wearer at about the level of the bottom of the rib cage or kidneys. All straps are adjustable in length for proper fitment to the wearer. The elongated back panel provides stability to the sensor from rotational displacement. The relatively high waist level of the chest strap provides security from vertical displacement of the sensor, and avoids interference with the waist belt appliance 50.

Referring to FIGS. 3B and 3C, waist belt appliances 50 and 50A respectively, have a belt panel 51, the center section 52 of which is fabricated of non-stretch material, and is configured with a sensor pocket 53, with mounting loop slots as described above, sized and suitable for snuggly securing either a sensor 10 or 10A. Belt straps 54 and 55 extend from left and right ends of belt panel 51 and are buckled together at the front of the wearer.

Referring to FIGS. 4A, 4B, and 4C, glove appliance 58 is configured with a backside strap 59, the end of which is threaded through loops 12 (FIGS. 4D and 5) of sensor 10 and secured by hook and loop material or other commonly known fastener means to glove appliance 58. As with the other appliances, the loop and strap means of attachment may in the alternative be a hard mechanical interface between a suitable structure incorporated into the back of the glove appliance and a mating structure on the sensor.

Referring to FIGS. 4A, 4B, 4C, and 4D, and sensor 10 in particular, the packaging of the battery, sensor, transmitter, and the internal circuitry for data processing, transmission, and for recharging the battery, is uniquely designed to: (1) minimize the package size and weight; (2) place the center of mass as close as possible to the contact surface side of the sensor to minimize inertial forces tending to rotate or displace the sensor within its appliance relative to the intended target area of the user's body; and (3) to optimize the location of the sensing elements within the package to be as close to the center of the sensor's footprint as practical for best intuitive alignment of the sensor over the target area. To this end, the sensor uses a stacked configuration which places the relatively thin battery (the heaviest component and majority mass of the sensor) at the bottom closest to and conforming to the curved shape of the underside or user contact surface, with the circuit boards and sensing elements above it, only slightly further outboard from the user.

Each sensor has a unique identifier that is encoded within the output data stream, for unambiguous identity during multi-sensor operation. While not strictly necessary, in typical systems sensors are mounted in their appliances on the body with a consistent, pre-determined orientation or "up" end direction, simplifying the calibration and data processing.

Referring to FIG. 4D, one embodiment of a wireless inertial sensor 10 of the invention consists of an enclosure having a bottom cover 14 and a top cover 28, within which is housed a lithium battery 16, electronics shelf 18, printed circuit board 20 with switch, battery charger circuitry, on/off button 22, sensor assembly 24 which includes the transmitter, and light pipe 26. The lithium battery 16 conforms to the curved shape of bottom cover 14. It is readily apparent that the mass of battery 16, a substantial portion of the sensor mass, is distributed across and close to bottom cover 14. This stacking arrangement with the battery at the bottom provides a very low center of gravity for the sensor, improving its resistance to rotational or sliding displacement within the pocket of the appliance or on the back of the hand during body motion. The flat, relatively thin battery shape permits the inertial sensor to be outboard of the battery and the sensor package to remain relatively thin.

As described above, referring to FIGS. 4B, 4D and 5, mounting loops 12 extend from bottom cover 14 and provide for mounting stability in two respects. Sensor pockets 43 and 53 (FIGS. 3A, 3B, and 3C) in vest and waist belt appliances are configured with slots (not shown but readily understood from this description) that receive mounting loops 12, providing a keying effect for proper insertion and positioning of the sensors within the pockets.

Referring to FIG. 5, this embodiment sensor is a wired inertial sensor 10A and consists of an enclosure having components analogous to those of sensor 10 (FIG. 4D), but the enclosure shape and configuration of components is adapted to use a conventional 9 volt battery positioned at one edge of the enclosure, accessible through battery door 15, rather than the stacked order of assembly of sensor 10.

Figure 6:
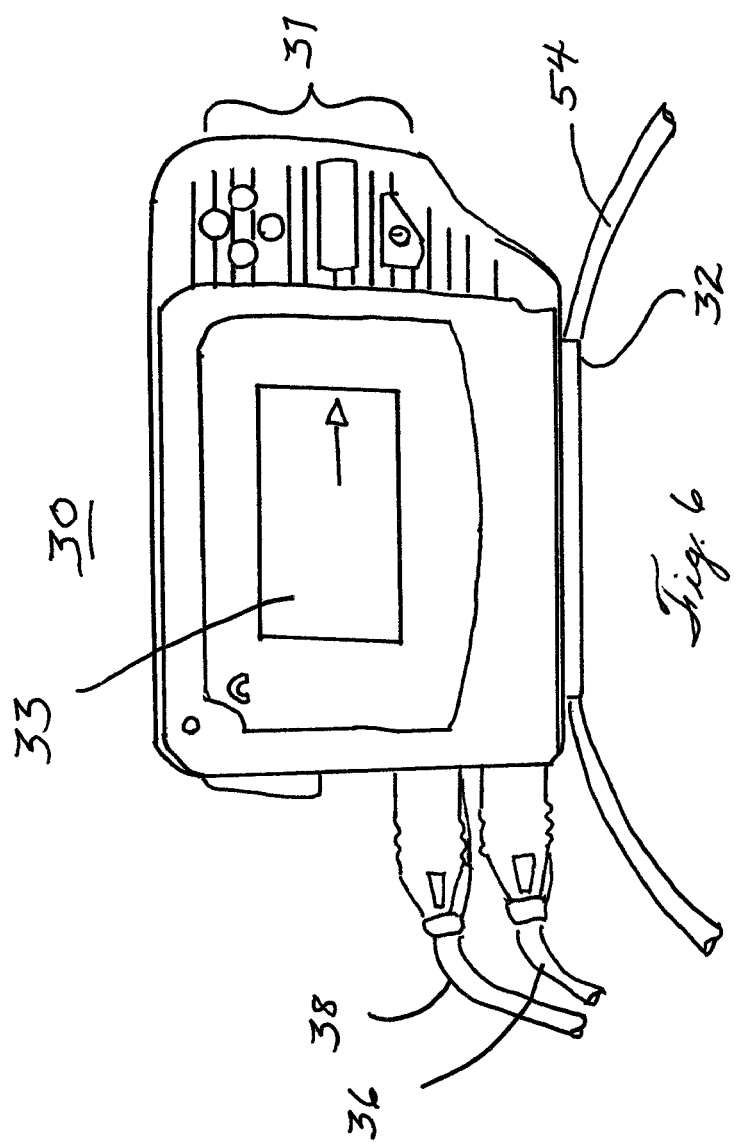
FIG. 6 is a front face view of a control module to which body sensors may be wired for wireless transmission to a receiver/computer system and/or local display of selected parameters of motion.

Referring to FIGS. 3C and 6, there is in one embodiment of the motion analysis system a control module 30 wired to sensors in sensor pocket 42 and 52 via cables 38 and 36 for receiving motion data. It has a hinged attachment 32 to belt 54 so that controls 31 and display 33 are easily viewable by the user. There is internal data processing capability and display driver for providing information directly to the user, and an integral wireless transmitter or transceiver for transmitting data to a motion analysis system 70 (FIG. 2), and/or receiving setup or other data or instructions from the motion analysis system.

Control module 30 is configured with a battery pack, hip sensor input, shoulder sensor input, micro computer, keypad, LCD display, USB connection, remote sensor and system transceiver capability, and optionally with a video game interface.

Figure 7:
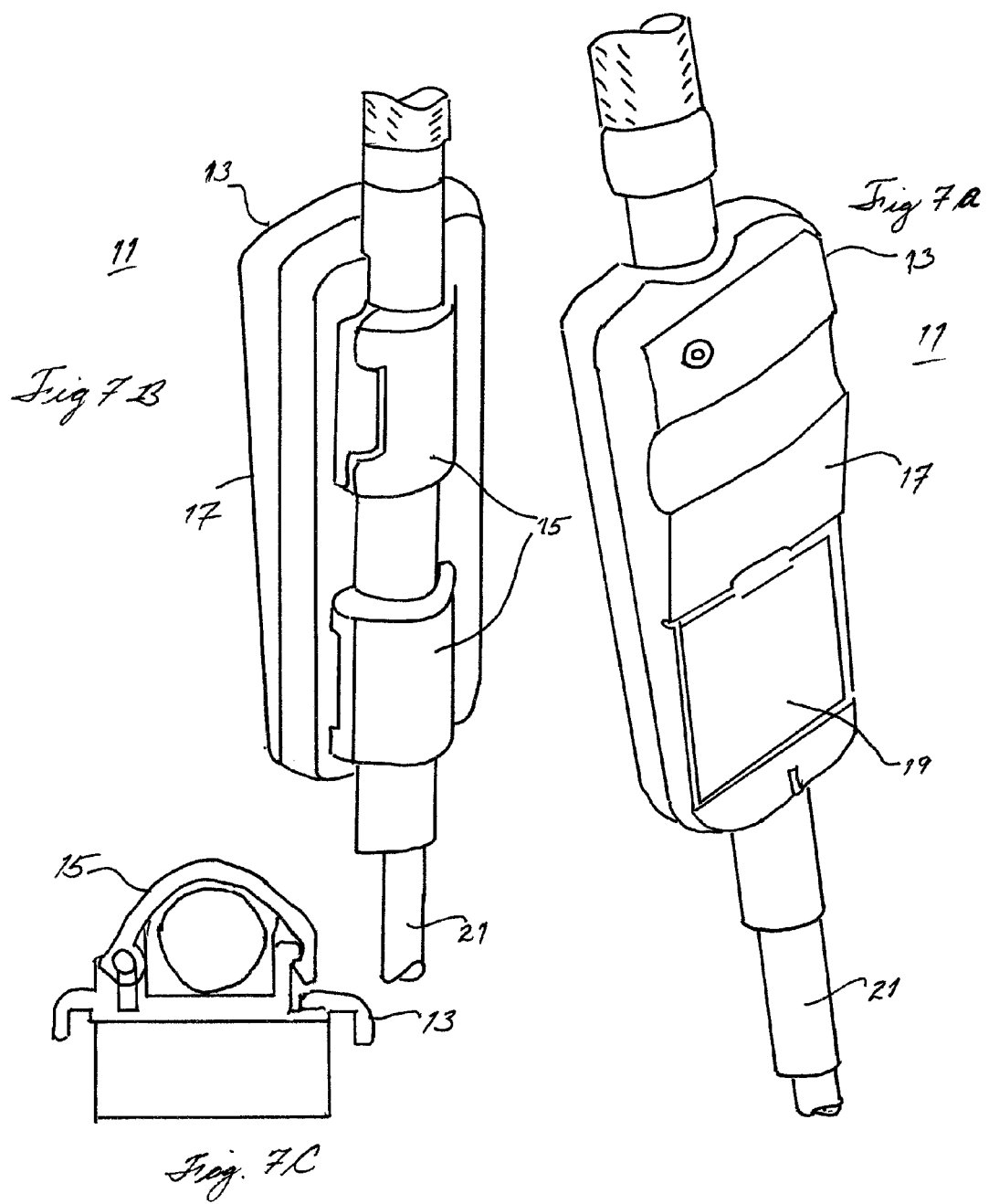
FIG. 7A is a front perspective view of a golf club sensor assembly, attached to the shaft of a gulf club.
FIG. 7B is a backside perspective view of the golf club sensor assembly of FIG. 4g.
FIG. 7C is a cross section view of the golf club sensor of FIG. 4g.

Referring to FIGS. 7A, 7B and 7C, there may in addition or in the alternative to the body worn appliances, a mounting appliance attachable to the tool or in this case golf club, for mounting a sensor. Alternatively, the mounting means may be incorporated into the sensor enclosure as in wireless club sensor 11, where the back cover 13 incorporates a latch mechanism 15 for securing sensor 11 to the shaft 21 of a golf club. Top cover 17 encloses the battery at its lower end, accessible via battery door 19, while the electronic circuitry and sensor elements are contained in the upper section closer to the grip of the club.

Figure 8:
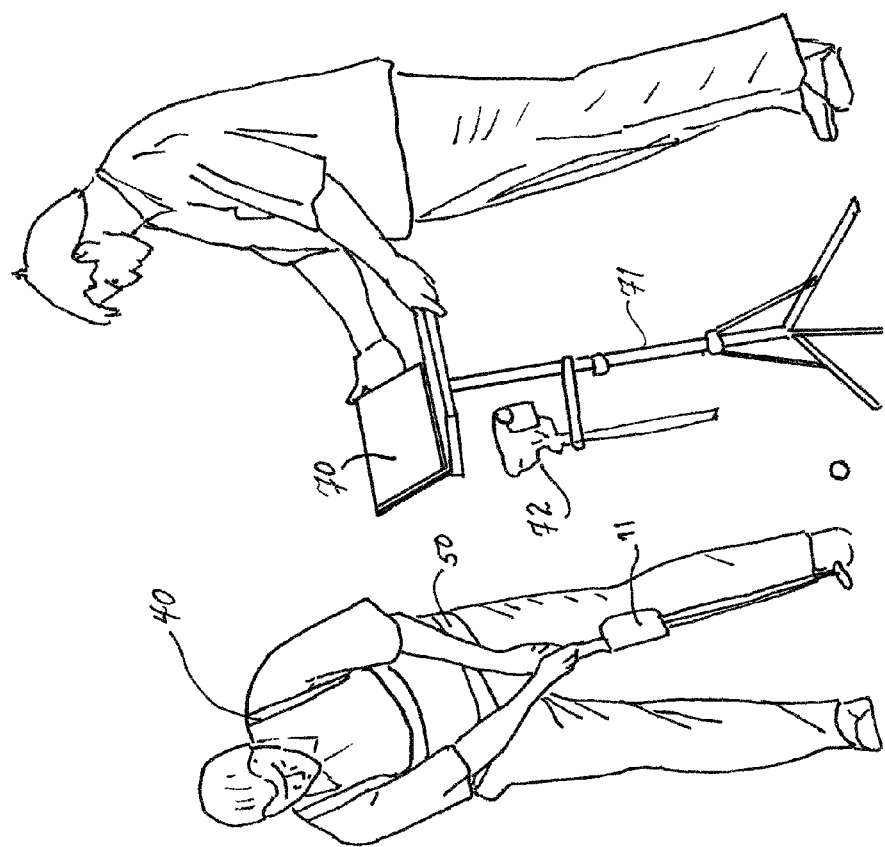
FIG. 8 is an illustration of one embodiment of the system and method of the invention in use, consisting of a golfer wearing vest and waist belt appliances mounted with inertial sensors and holding a golf club with an inertial sensor mounted just below the grip of the club, standing adjacent to a stand supporting a video camera directed at the golfer and an associated receiver and processing computer with keyboard and display, the display being viewed by an instructor.

Referring now to FIG. 8, there is illustrated of one embodiment of the system and method of the invention in use, consisting of a golfer wearing vest appliance 40 and waist belt appliance 50 which are each equipped with a wireless inertial sensor as described above. The golfer is holding a golf club with an inertial sensor 11 mounted just below the grip of the club, standing adjacent to a stand 71 supporting a video camera 72 directed at the golfer and an associated receiver and processing computer system 70 with keyboard and display, the display being viewed by an instructor.

The camera positions and direction with respect to the golfer's position, size and posture are carefully aligned with respect to the test site from one or the other or both of at least two positions: a first camera position at a specific down line angle, height, and lateral position or offset, and another camera position for face on angle, including height and offset. Correct camera positioning enables placement of an overlay in the video display that includes vertical and horizontal alignment lines representing center of alignment and center of balance. There may be multiple cameras on additional stands oriented to capture the motion from different directions and different heights and offsets, and some or all may be positioned carefully to support the further use of overlays of alignment lines relating to the golfer's position, size, posture, and expected motions, so as to make motions and deviations in alignment very apparent in subsequent video presentations of the swing motion.

Stated more generally, prior to testing, it may be required to select and define a test site to have at least one motion reference point; to then position the video camera to be directed at the test site at a pre-defined angle of rotation around the point or test site, a specific height relative to the reference point, with a specific angle of elevation and lateral offset with respect to the reference point. Thereafter a video test signal of the test site and reference point is sent to the computer-driven display screen and an overlay is inserted onto the computer-driven display screen corresponding to the reference point, from which specific motions are more easily observed.

The processing computer or PC of system 70 performs relational calculations on the parameters received from the various sensors, thereby allowing computation of various golf-related parameters of interest. As an example, the PC can calculate club-face angle or the angle through which the golfer turns his or her shoulders while swinging the golf club. Such parameters are referred to here as performance or alternatively diagnostic parameters, to distinguish them from the rate or position parameters transmitted by the sensors to the PC.

In a golf swing motion analysis system in particular, rate and position motion data are typically processed by the application software into performance or diagnostic parameters relating to the golfer's body segment performance, including: hip velocity (degrees per second); hip rotation (degrees negative and positive); shoulder velocity (degrees per second); shoulder rotation (degrees negative and positive); club release (degrees per second); club speed (miles per hour); club face rotation (degrees open/closed); club path (degrees inside or outside of club's address position); hip linear movement (centimeters left or right of neutral address); hip and shoulder separation (time difference between maximum hip, shoulder, and club velocity); flexion/extension of hip segment (centimeters traveled along z-axis); and kinetic link. These parameters are further extrapolated to yield a predicted resulting "ball in flight" performance of parameters: spin (degrees per second); launch angle (degrees); carry distance; roll distance (yards); total distance (yards); distance traveled off line (yards right or left); ball flight character (fade, draw, hook, slice, push, pull, straight); and PTI or power transfer index.

This processed information is reported to the golfer in a unique, synchronized, multi-format presentation of the swing motion that is available in real time and/or playback mode for optimal user and instructor assimilation.

Figure 9:
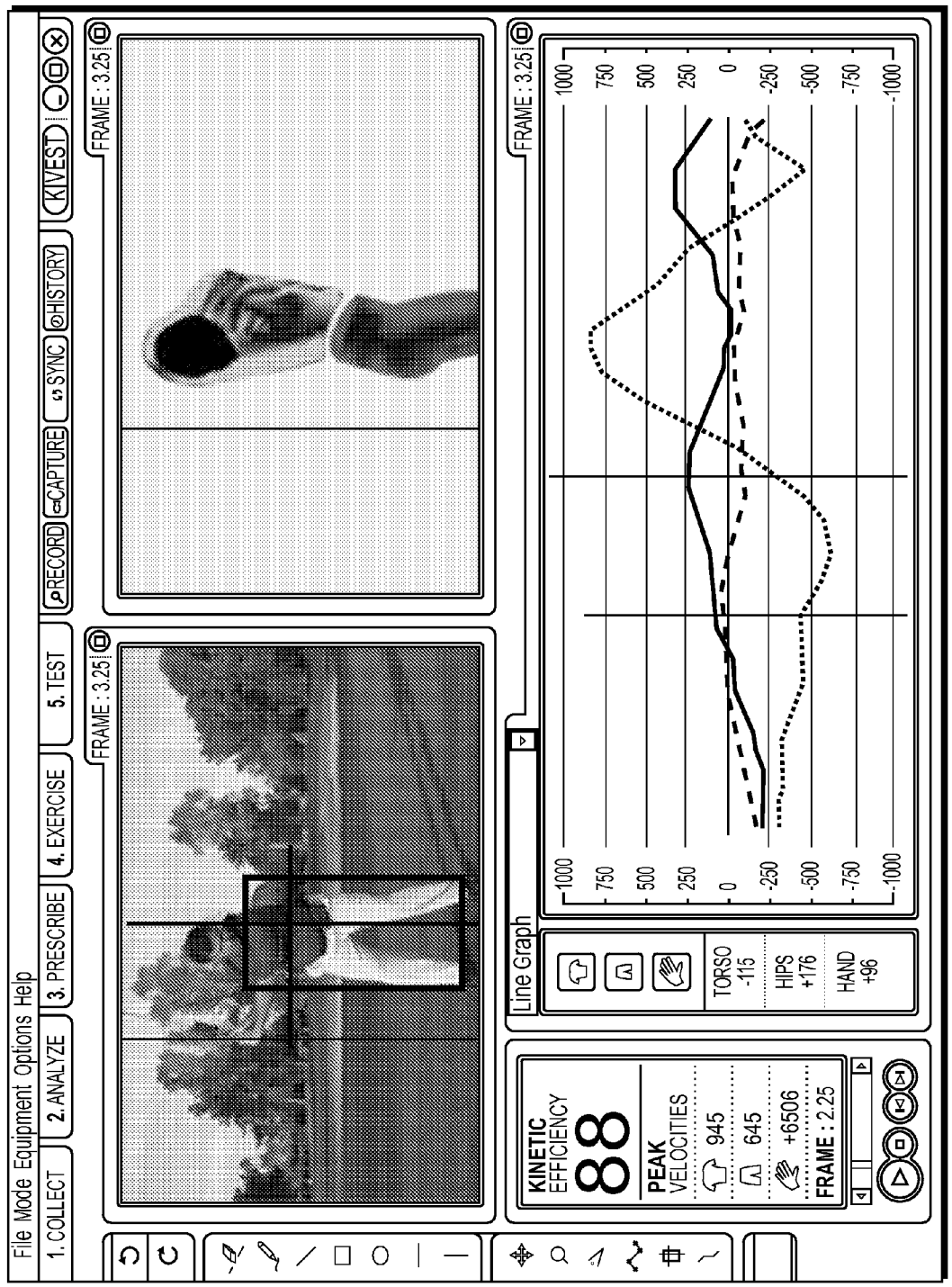
FIG. 9 is a screen shot of the composite display of the invention, incorporating three formats of feedback: a live video feed of the golfer in the upper left portion of the display, an animation of the golfer in the upper right portion of the display that is color coded to distinguish major body segments; and in the lower portion of the display a motion data time line graph tracing hip, shoulder and hand motions in a multi-colored trace.

FIG. 9 is a screen shot of the synchronized, composite display of the invention, incorporating three formats or forms of feedback. In a real time feedback or "biofeedback" mode, there is a live video feed of the golfer, typically a face on or side view, presented in the upper left portion of the display although it may be placed elsewhere in the display, in which the alignment lines are applied during a set up phase, are stationary and the motion with respect to the alignment lines is readily apparent.

A multi-color animation of the golfer, generated from the inertial sensor motion data, is presented in the upper right portion of the display, although it may be positioned elsewhere in the display. The animation may be color coded to distinguish major body segments, e.g. the shoulders segment versus the hips segment. The animation may be oriented to view the swing motion from any useful angle, depending on what aspect or component of the swing motion is being scrutinized at the time.

In the lower portion of the display a motion data time line graph traces hip, shoulder and hand motions in a multi-colored trace, although it may be positioned elsewhere in the display. The graph may present simply the component motion data from the instant swing motion, and demonstrate graphically the coordination between hips, shoulders and hand motion; or it may present a comparative trace of the present motion or component of motion compared to a prior motion or an expert motion in order to illustrate the degree of deviation and required improvement to achieve a desired performance level.

Figure 10A:
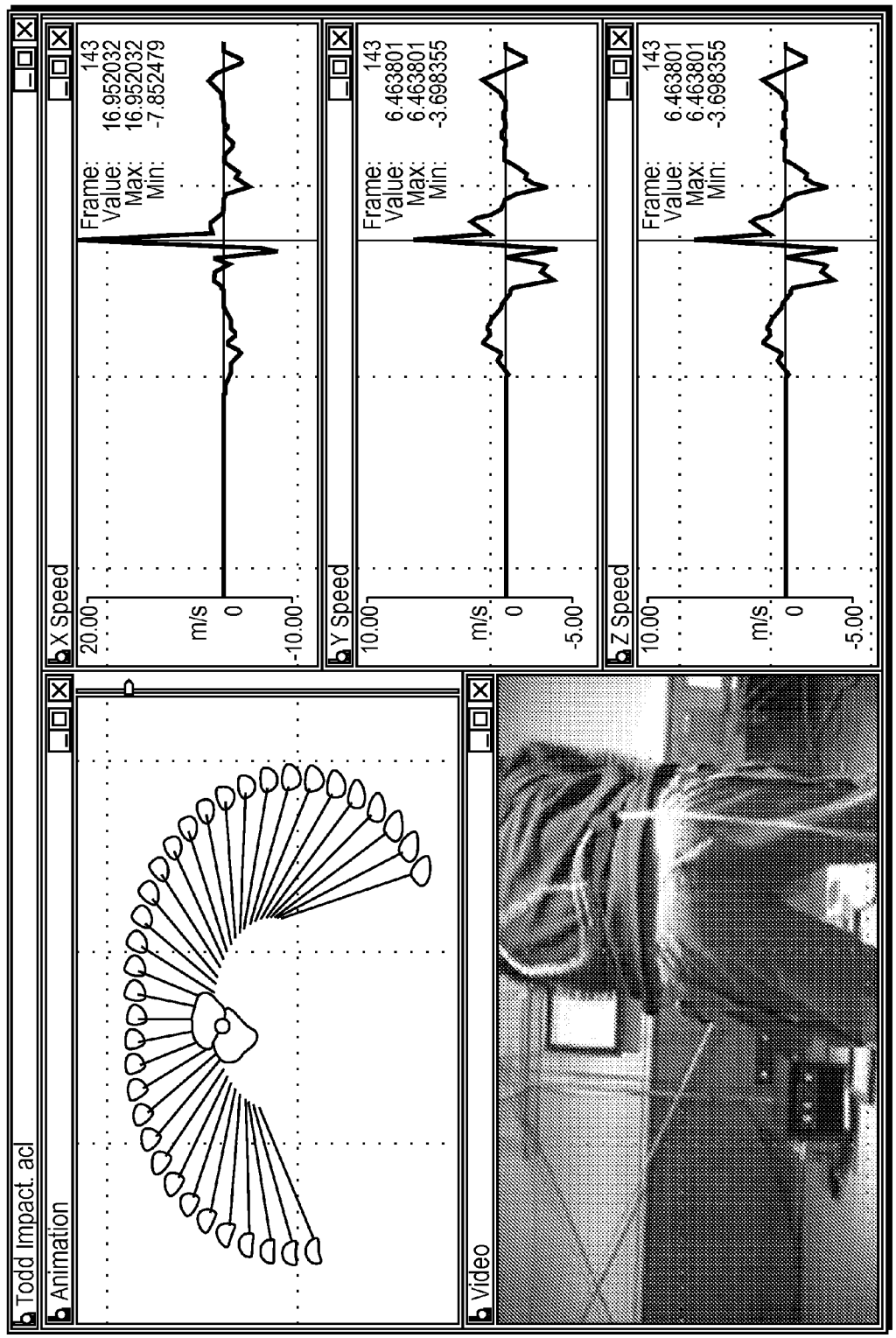
FIG. 10A is a screen shot of a composite display of the invention, incorporating three formats of feedback: a live video feed of the golfer in the lower left side portion of the display; a time-stepped animation of the club swing indicating the plane of the club swing and the hand orientation during a swing motion; and three motion data time line graphs showing the club speed in three axis.

Referring to FIG. 10A, another example of the composite, multi-format, synchronized display is a screen shot of a composite display of the invention, incorporating the three formats of feedback of FIG. 9: a video record of the golfer this time in the lower left side portion of the display; a stepped frame animation of the club swing indicating the plane of the club swing and the hand orientation during a swing motion; and three motion data time line graphs showing the club speed in three axis.

The stepped frame animation is a useful device for illustrating the plane, path or arc of a motion or component of motion, and is a further enhancement of the presentation. Selected positions of a point or object or portion of the video screen are retained as the video progresses so as to show the path leading up to the present position. The stepped aspect of the presentation can be done as function of time, or of linear or angular displacement of the object or point of interest, whichever better serves to illustrate the path of motion best for the viewer.

Stated more generally, the multi-color, three dimensional animation representing the motion of at least one color-coded body segment created from motion data may include or be in some embodiments a stepped frame animation where selected positions of an object in motion are retained in subsequent frames of the animation such that a motion track of the object is apparent to a viewer. The retained positions may be programmed to be selected on the basis of time, position, speed, or acceleration of the object in motion.

The orientation on the screen of these multiple forms of simultaneous presentation may be varied. There may be additional information as well, space permitting. A composite presentation of video, animation, and motion data graphs enhances the user's ability to quickly assimilate and appreciate the subtle differences at the component level of the swing motion, between his current performance and the desired performance. A multi-dimensional presentation of the swing performance can be watched in real time, in an instant replay mode, or in a later review.

Figure 10B:
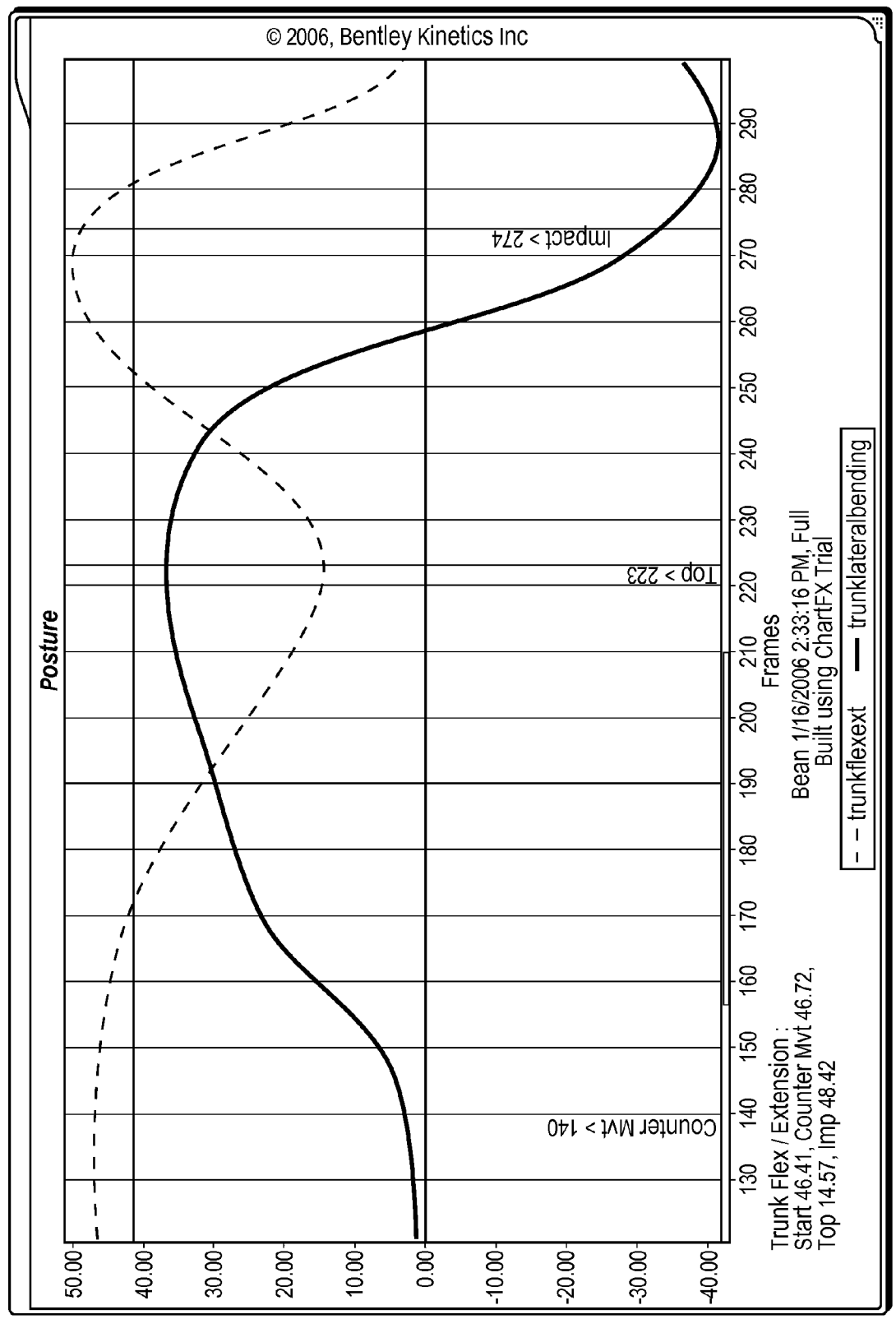
FIG. 10B is a line graph indicating posture with respect to trunk flex extension and trunk lateral bending versus time during a swing motion.
Figure 10C:
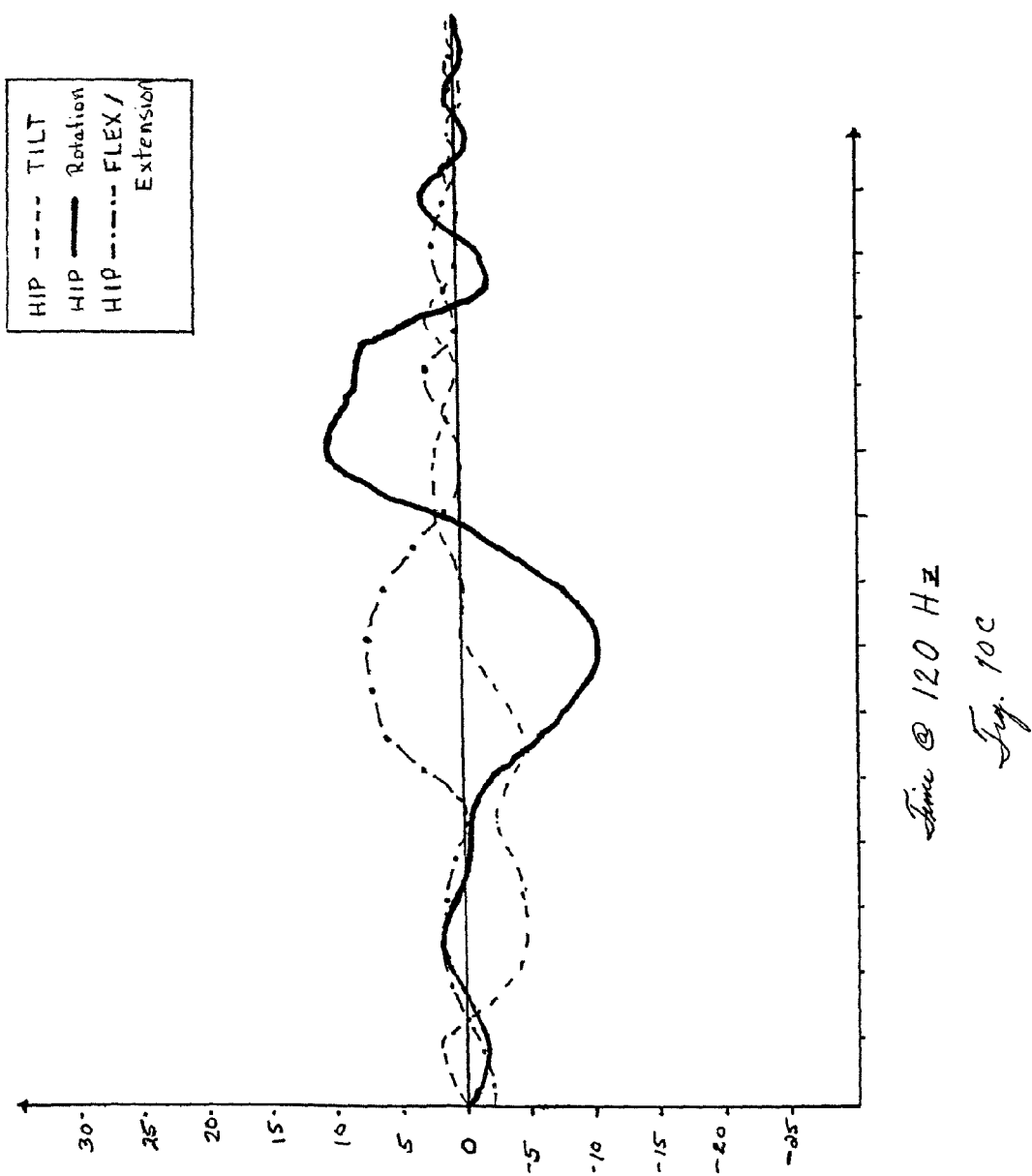
FIG. 10C is a line graph indicating degree of pivot during a swing motion.
Figure 10D:
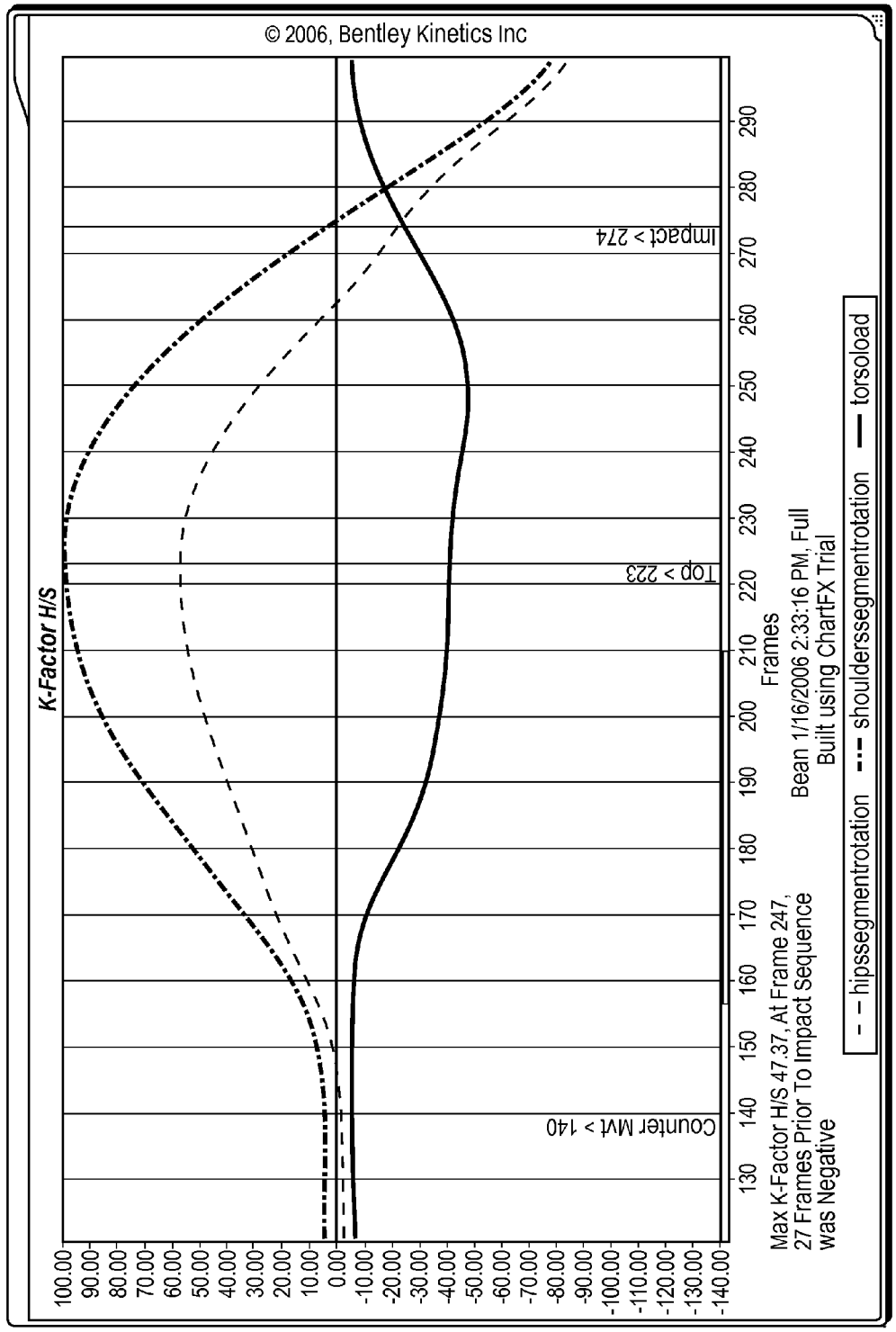
FIG. 10D is a line graph indicating degrees of hip segment rotation, shoulder segment rotation, and torso load during a swing motion.
Figure 10E:
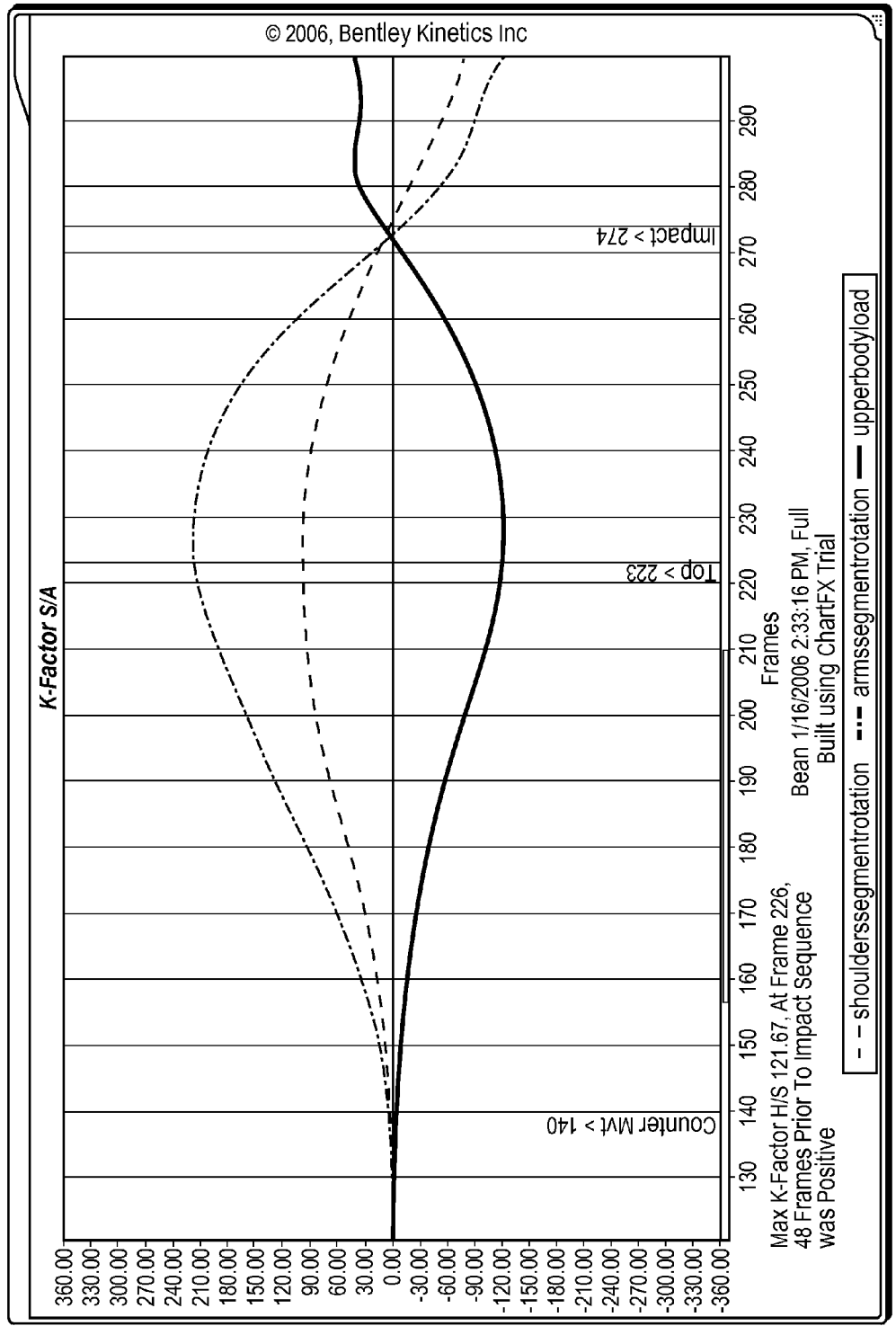
FIG. 10E is a line graph indicating degrees of shoulder segment rotation, arm segment rotation, and upper body load during a swing motion.
Figure 10F:
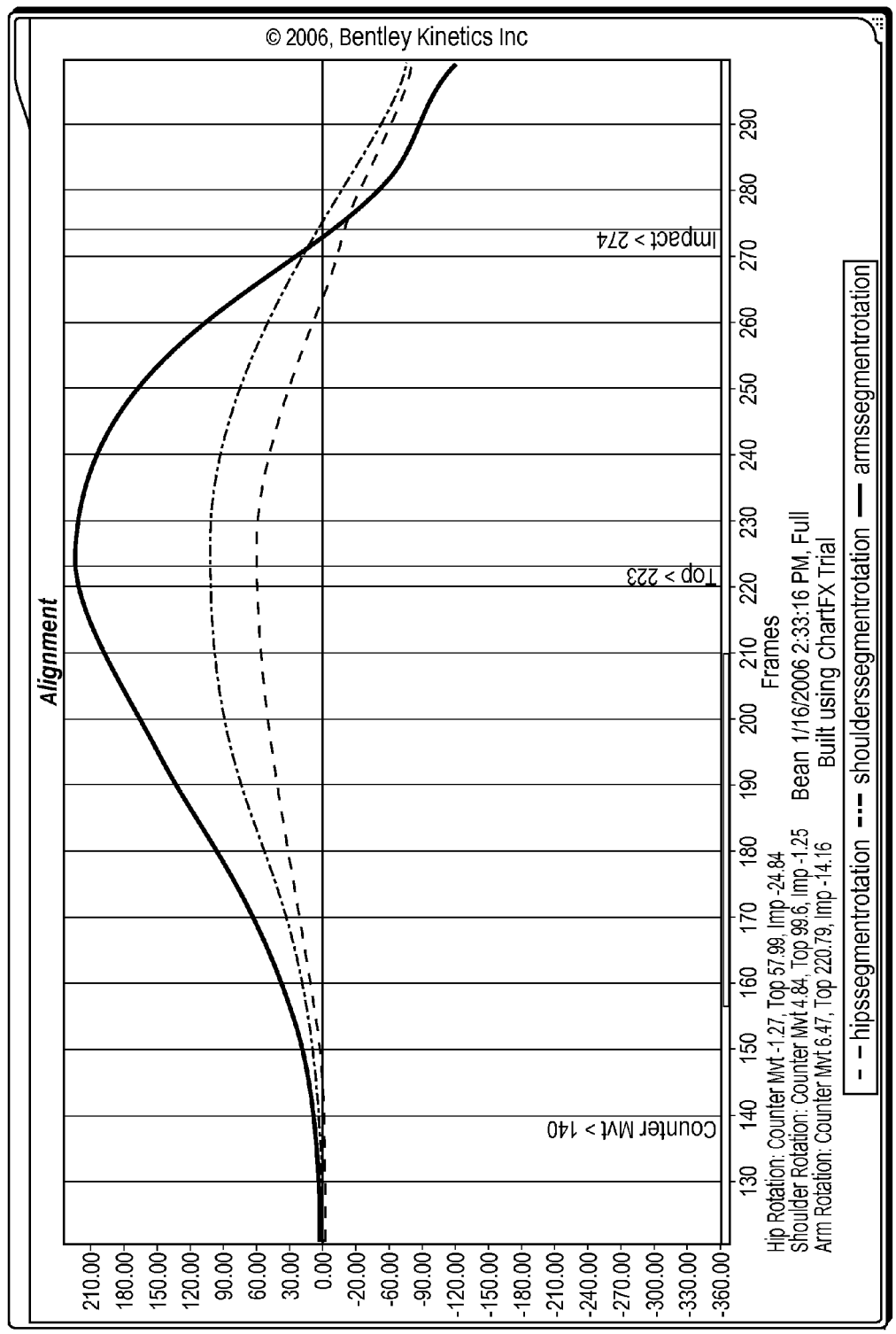
FIG. 10F is a line graph indicating alignment of hip segment rotation, shoulder segment rotation, arm segment rotation versus time during a swing motion.
Figure 10G:
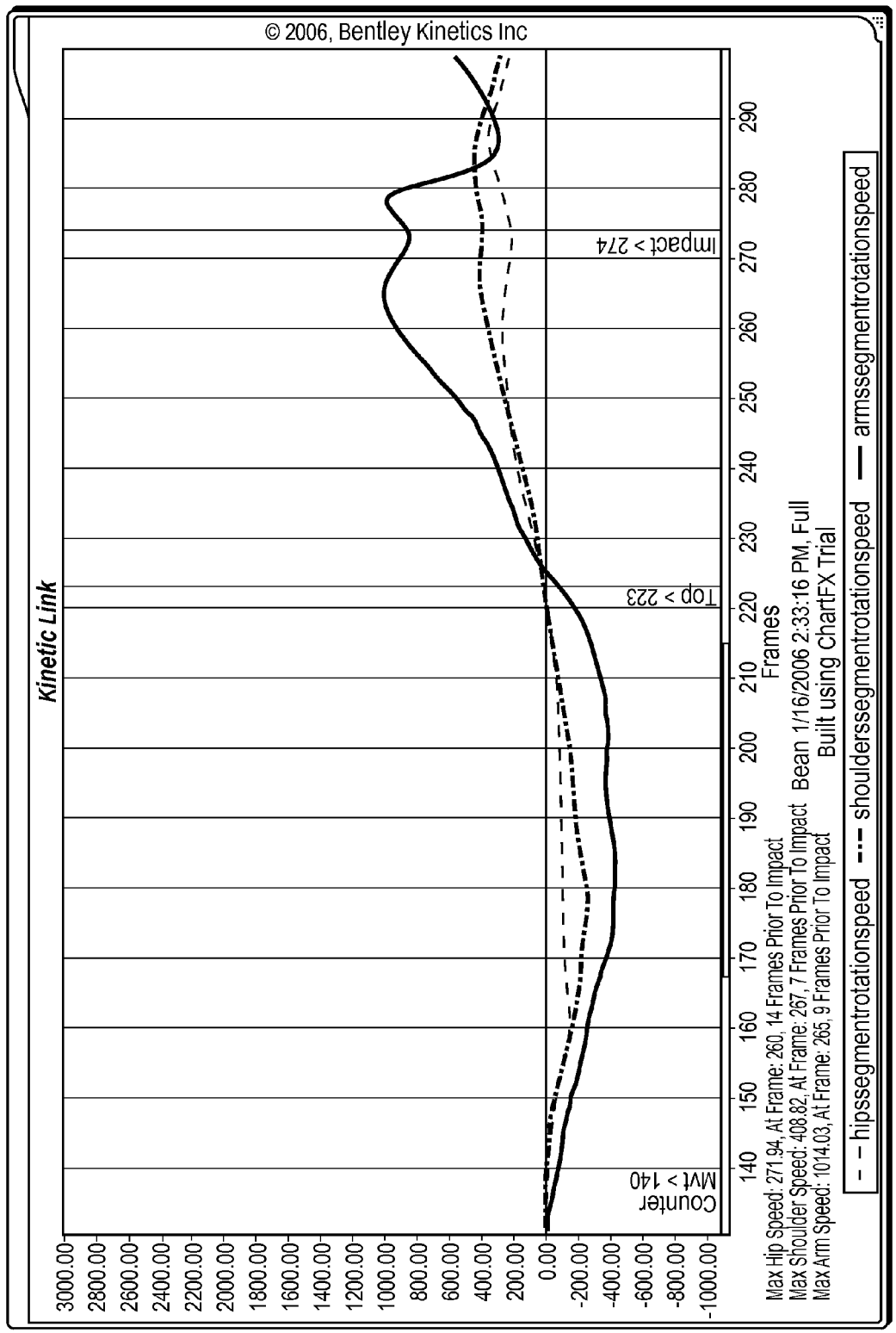
FIG. 10G is a line graph indicating hip segment rotation speed, shoulder segment rotation speed, and arm segment rotation speed during a swing motion.

The system 70 also offers alternative and supplemental forms of presentation or "report" of the swing performance. Expanded graphs, for example, help clarify the timing of components of motion, as well as the amplitude. For example FIG. 10B is a line graph indicating posture with respect to trunk flex extension and trunk lateral bending versus time during a swing motion. FIG. 10C is a line graph indicating degree of pivot during a swing motion. FIG. 10D is a line graph indicating degrees of hip segment rotation, shoulder segment rotation, and torso load during a swing motion. FIG. 10E is a line graph indicating degrees of shoulder segment rotation, arm segment rotation, and upper body load during a swing motion. FIG. 10F is a line graph indicating alignment or coordination of hip segment rotation, shoulder segment rotation, arm segment rotation motions versus time during a swing motion. FIG. 10G is a line graph indicating hip segment rotation speed, shoulder segment rotation speed, and arm segment rotation speed during a swing motion.

Figure 11:
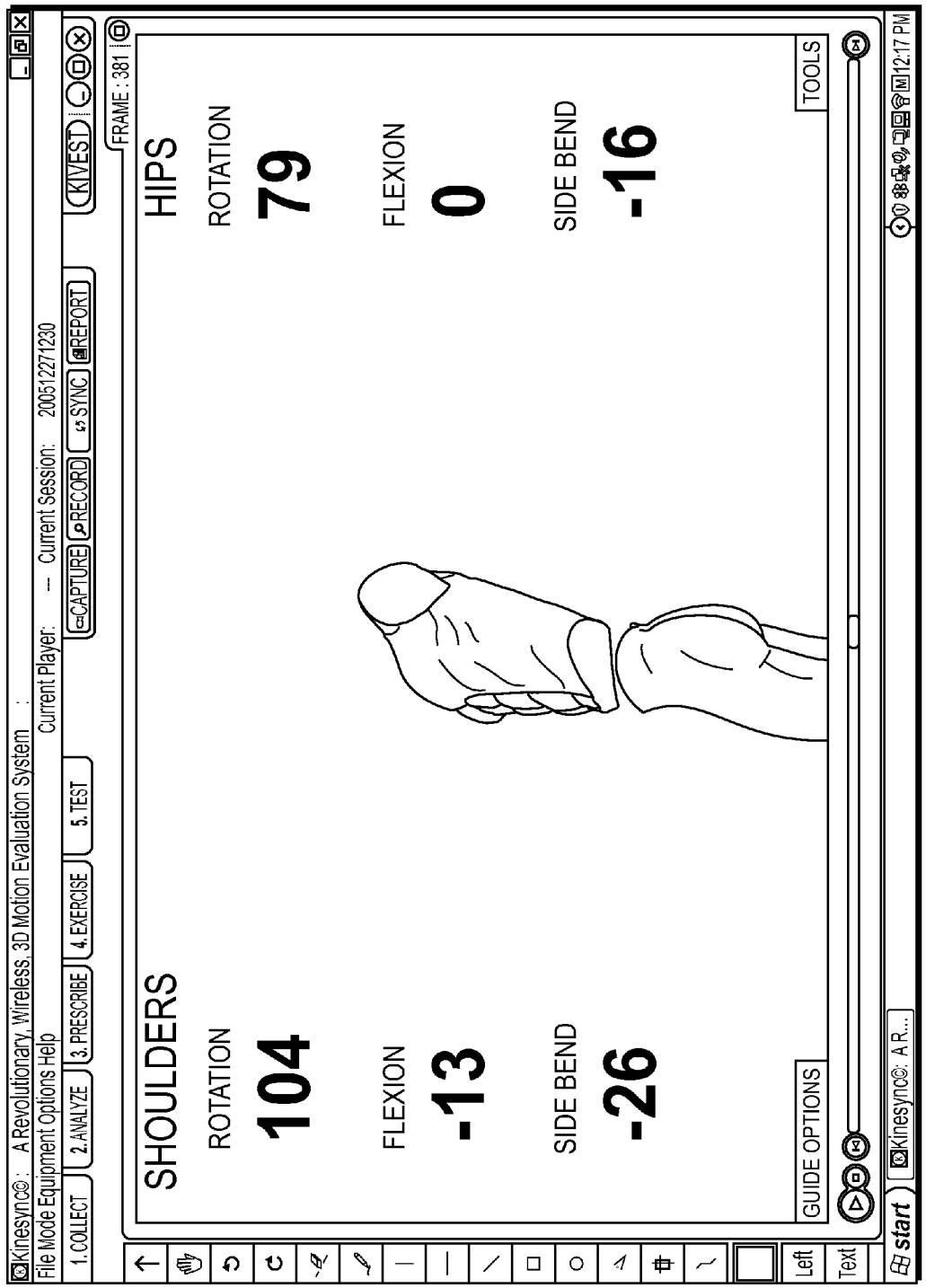
FIG. 11 is a screen shot of the multi-color animation illustrating the color distinction between the shoulder segment and the hips segment of the animation.

The animation capability of the system, driven by the inertial sensor inputs, offers additional opportunities for presenting more detailed illustrations of the swing motion in real time or playback mode. For example, FIG. 11 is a screen shot of a multi-color animation illustrating the color distinction between the shoulder segment and the hips segment of the animation. This makes for easy and quick distinction between these components of the full swing motion. The numerical value of peak or range of rotation, flexion, and side bend are posted left and right of the animation for calibrating the user's perspective of the animation motion.

Figure 12:
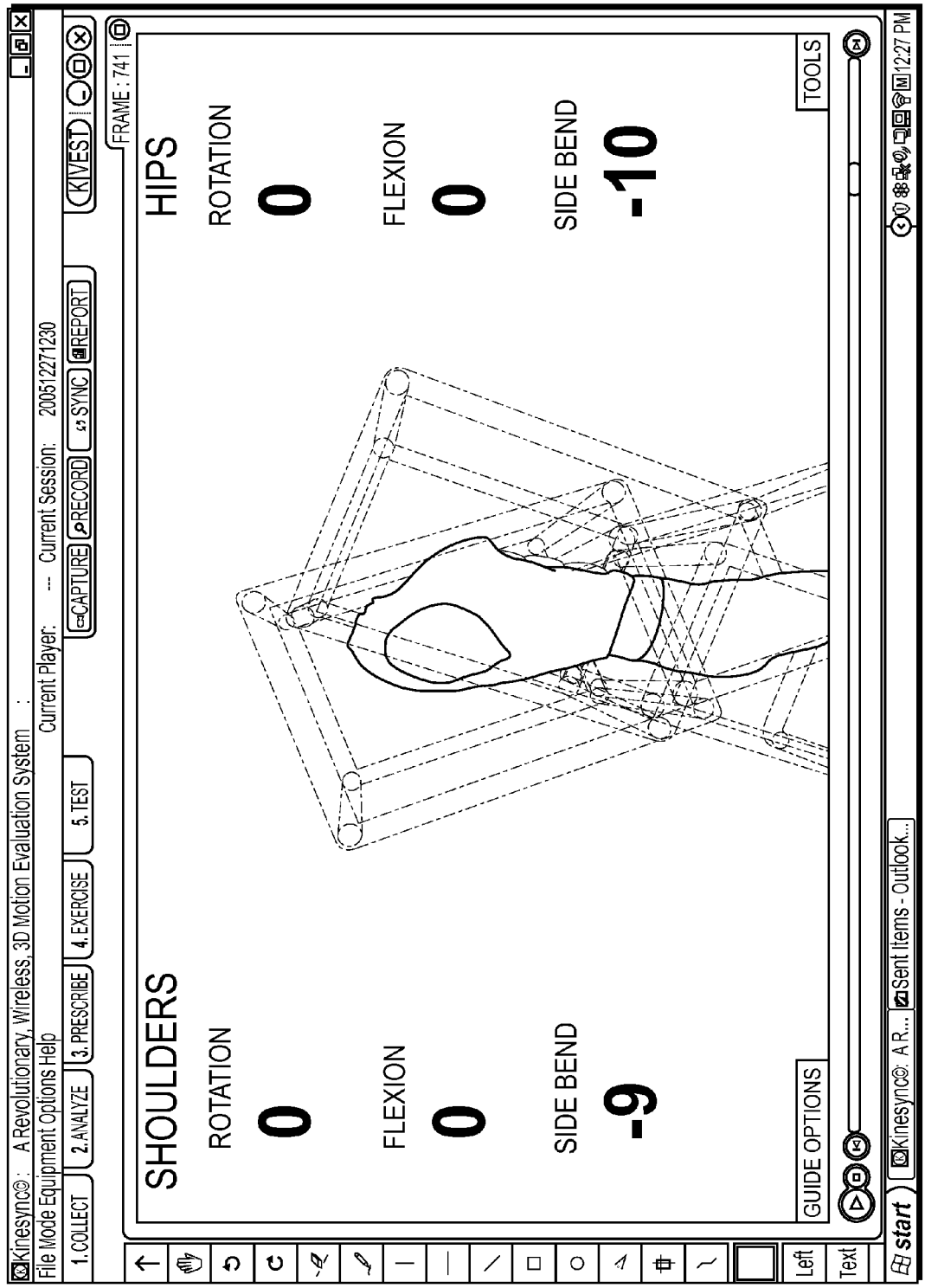
FIG. 12 is a screen shot of a multi-color animation illustrating the cage by which user settable parameters for lateral bending during swing motion are made apparent to the golfer as real-time feedback.

The animation capability provides yet a further training tool in the form of animated "cages" or scalable limits of selected parameters that cage the animated figure and illustrate the golfer's movement within the three dimensional frame. FIG. 12 is a screen shot of a multi-color animation illustrating the box or cage by which user settable parameters for lateral bending during swing motion are made apparent to the golfer for real time feedback. The processing computer 70 can create an instantly apparent change to the display, for example by turning the background orange for close calls and red for actual violation of the cage parameters during a swing motion.

Figure 13:
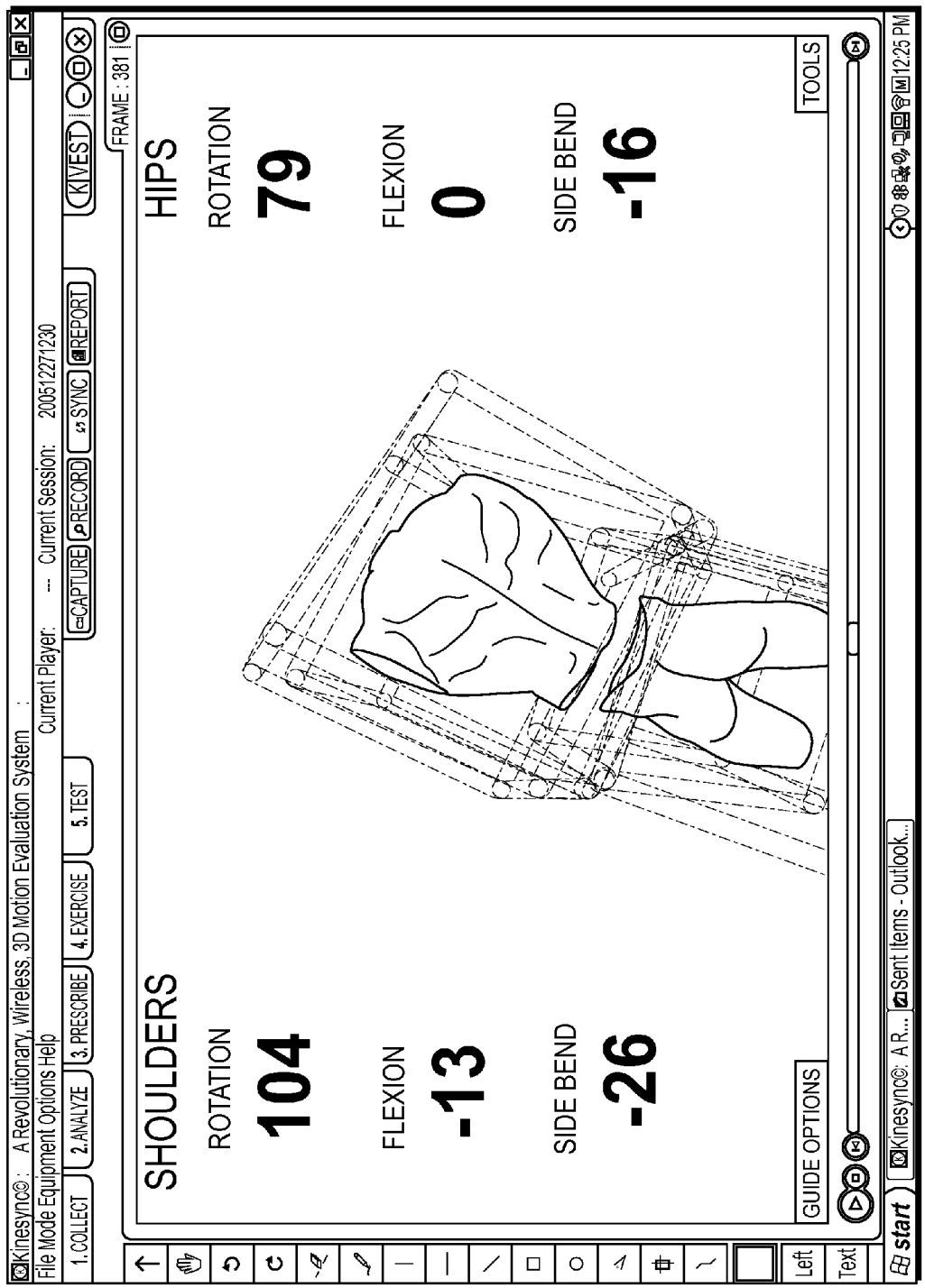
FIG. 13 is a screen shot of a multi-color animation illustrating the cage by which user-settable parameters for flexing during the swing motion are made apparent to the golfer as real-time feedback.
Figure 14:
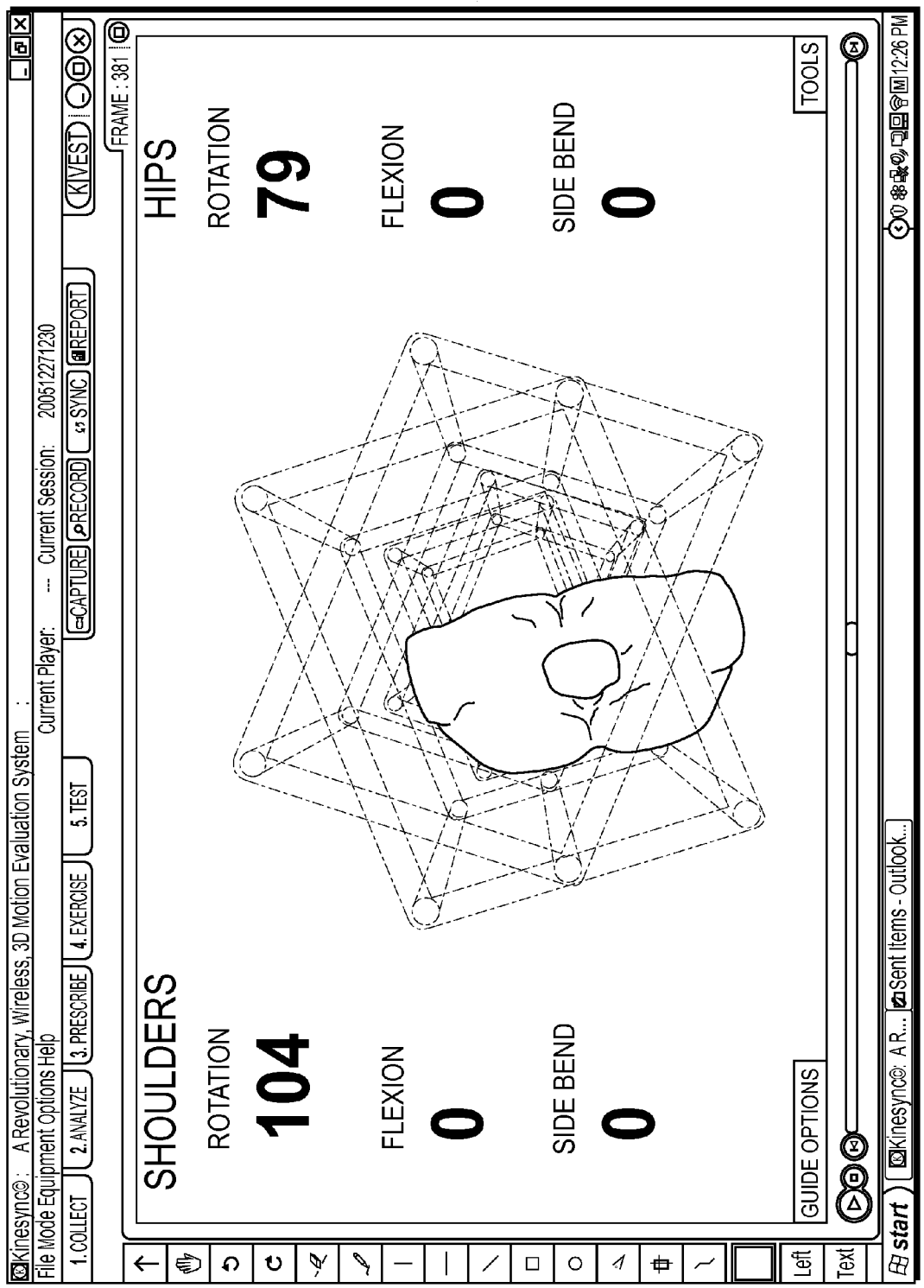
FIG. 14 is a screen shot of a multi-color animation illustrating the cage by which user-settable parameters for rotation during the swing motion are made apparent to the golfer as real-time feedback.

Further examples of the power of motion data animation as part or all of the presentation or "report" part of the methodology follow. FIG. 13 is a screen shot of a multi-color animation illustrating the three dimensional grid or open frame by which user-settable parameters for flexing during the swing motion are made apparent to the golfer as real-time feedback. FIG. 14 is a screen shot of a multi-color animation illustrating the "box" by which user-settable parameters for rotation.

Figure 15:
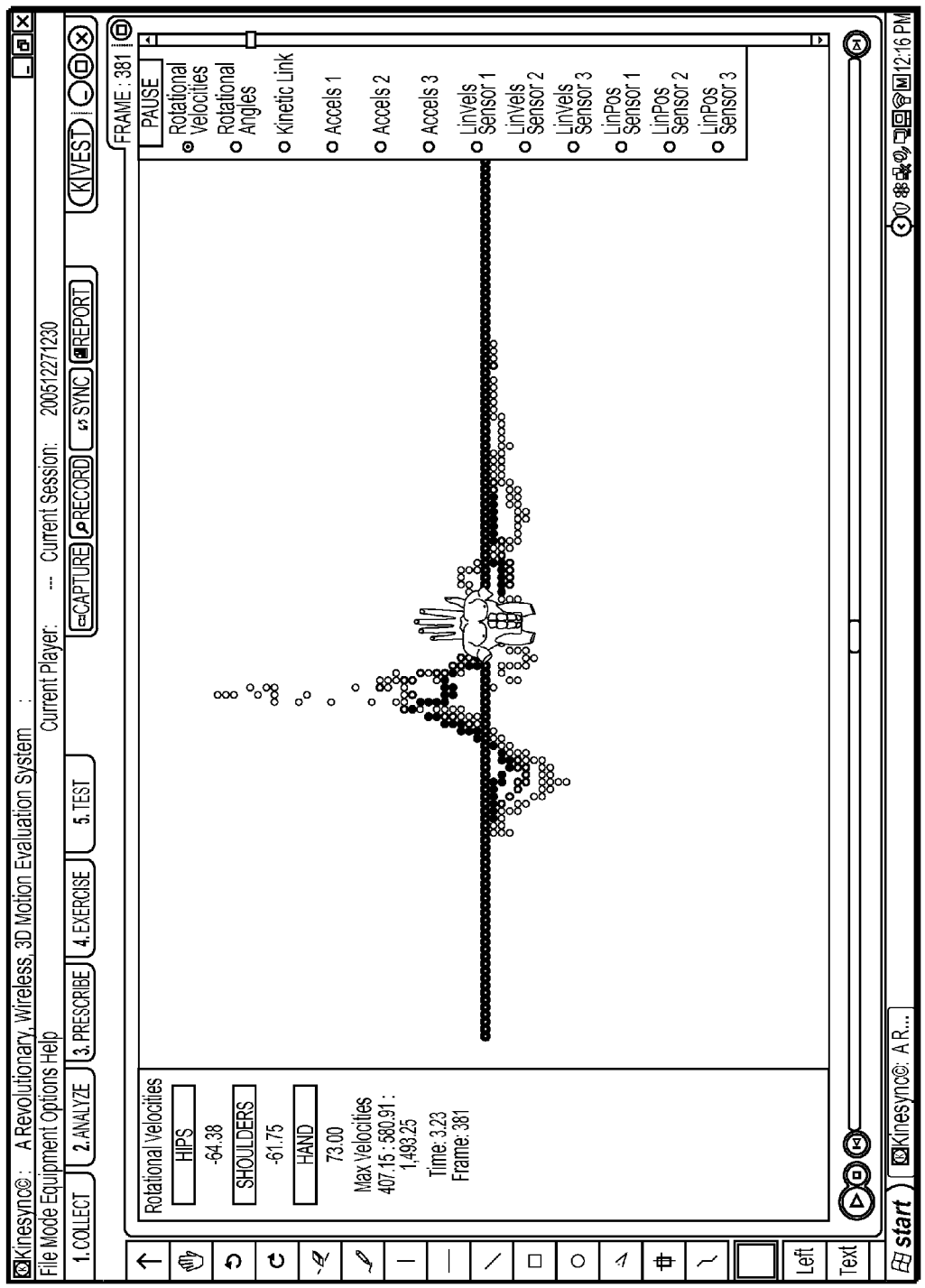
FIG. 15 is a screen shot of a multi-color line graph illustrating the coordination in time and amplitude of the rotational velocities of the hips, shoulders, and hand of the golfer during the swing motion.

The animation capability of the system can also be used to present an enhanced version of the time line traces or graphs. FIG. 15 is a screen shot of a multi-color line graph illustrating the coordination in time and amplitude of the rotational velocities of the hips, shoulders, and hand of the golfer during the swing motion.

It should be noted that although FIG. 11 through 15 are illustrated here as full screen shots; these and other animations of the motion data and settable parameters are within the scope of the invention and can be presented in the multi-format form of FIG. 9, with synchronized video and graphs.

It is a goal of the invention to provide an objective, consistent analysis of each performance. The methodology of the invention depends on capturing motion data, processing it into the described parameters relating to body segments and components of the motion, providing a quantitative analysis of each component of motion, and then summing the scores for each component of motion so as to produce a unitary number or "kinetic index" for the performance as a whole. One embodiment of a system 70 for golf swing motion analysis processes motion data against benchmark values to produce a value on a uniform index scale of 0-50 for each of the following primary performance parameters: sequence, speed, stability, mobility, transfer, timing, club performance, and club accuracy. These values are summed in a pre-determined order to arrive at a unitary number representing the kinetic index for the total performance on a scale of 0-100, as described further below.

Figure 16:
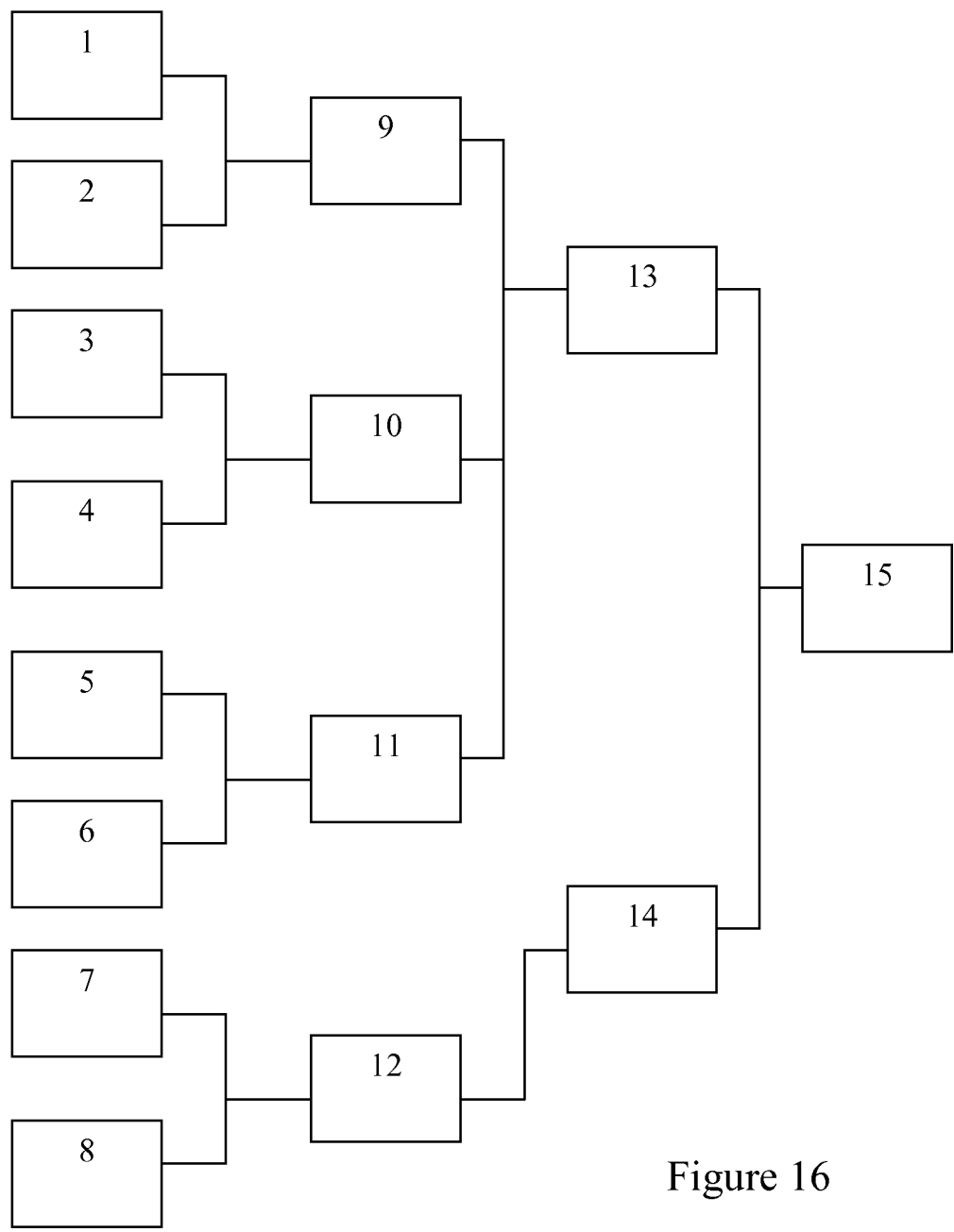
FIG. 16 is a simplified representation of a multi-step process for the reduction of multiple primary performance parameters to a fewer number of secondary performance parameters, hence to respective body and club performance factors, and finally to a single kinetic index reflecting an objective evaluation of the total performance of a swing motion.

Objectivity and repeatability of the system for motion analysis depends on a consistent process that examines and gives weighted consideration of all relevant aspects of the motion in calculating a final performance factor or kinetic index. Referring now to FIG. 16, one aspect of the methodology of this embodiment is illustrated in an objective, repeatable, computer-automated reduction of the basic or primary performance parameters 1-8 measured by system 70 against pre-selected benchmark values, into a single kinetic index. The system uses a multi-step process that sums the primary parameters into secondary parameters 9-12, then into body performance factor 13 and club performance factor 14, and finally merges these values into kinetic index 15, a quantification of the overall performance value of the swing motion being analyzed.

The FIG. 16 performance parameters are explained below:

Primary Parameters:

1. Sequence: This parameter relates to the degree of timing and coordination of the rotational velocities of hips, shoulders and arms during the swing motion. For example, at 120 frames per second, the target or benchmark standard sequence for a golf swing motion is assumed to have maximum hip rotation velocity occur at 36 frames before maximum shoulder rotation; which should occur at 24 frames ahead of maximum arm rotation; which should occur at 16 frames ahead of the club impact on the ball. The total deviation in frame count from the pre-established or assumed ideal sequence for all segments is inversely weighted against a total maximum score or ideal performance index for the sequence parameter of 50, yielding a relatively lower score for respectively larger deviations.
2. Speed: This parameter relates to the maximum peak rotational velocity of each body segment. The benchmark is set at: 400 degrees/second for hip rotation; 800 degrees/second for shoulders rotation; 1600 degrees/second for arms rotation; and 3200 degrees/second for club rotation. The sum of the differences is weighted inversely against a maximum score of 50, yielding a relatively lower score for respectively larger differences.
3. Stability: This parameter relates to the orientation of the hip segment and shoulder segment in relation to the spine. It is measured in degrees. The benchmark for hips, shoulders, and arms are all 0 (zero). Again, the sum of the differences is weighted inversely and scaled against a maximum index of 50.
4. Mobility: This parameter relates to the relative range of angular rotation of hips, shoulders, arms around the spine. The benchmark is that they be equal. The sum of the differences are weighted inversely and scaled against a maximum index of 50.
5. Transfer: This parameter relates to the sum of the ratio of angular momentum of the hips to the shoulders, and hence to the arms. The measured transfer ratio is scaled against a benchmark maximum ratio of 6 and equated to a maximum index of 50. For example, using benchmark values, if 400 degrees/second of hip rotation produces 800 degrees/second for shoulders rotation, that is a transfer ratio of 800/400=2.0. Then if 800 degrees/second shoulders rotation results in 1600 degrees/second for arms rotation, and 3200 degrees/second for club rotation, then those transfer ratios are also 2.0 and 2.0 respectively; the sum of which is 6.0. A lesser actual score is divided by 6 and multiplied by 50 to generate a base-50 index score.
6. Timing: This parameter relates to the difference in time or coordination of maximum rotational velocities of hips, shoulders, and arms in time. The scoring is based on the delta or difference in timing in the manner described above, scaled against a maximum index of 50.
7. Club Performance: This parameter relates to the linear acceleration of the club, added to peak angular release velocity. The benchmark is 300 mph (miles per hour) for linear acceleration and 400 degrees/second of angular velocity. The simple sum, 700, is equated to a maximum performance index of 50, and the measured value scored accordingly.

8. Club Accuracy: This parameter relates to the three dimensional movement of the club on the ball and is graded on the velocity of the straight-on axis less the velocities in each of the orthogonal axis, in miles per hour. The total is compared to a benchmark and the result scaled to a maximum performance index of 50.

Second Order Parameters

The primary parameter scores 1-8 are reduced in a first step by a simple summing of related parameters as follows:

9. Sequence & Speed: the sum of the individual indexes of sequence 1 and speed 2 above, having a maximum index of 100.
10. Stability & Mobility: the sum of parameters 3 and 4 as above.
11. Transfer & Timing: the sum of parameters 5 and 6 as above.
12. Club Power Accuracy: the sum of club performance 7 and club accuracy 8 indexes.

These second order parameters are further reduced to a body performance factor 13 and a club performance factor 14 as follows:

13. Body Performance Factor: the sum of parameters 9, 10, and 11 divided by 3, having a maximum index of 100.
14. Club Performance Factor: simply the club power accuracy 12 index brought forward.

The body and performance factors 13 and 14 are summed and divided by 2 to yield the:

15. Kinetic Efficiency Index: having a scale of 0 to maximum 100.

It will be appreciated that the pre-selected benchmark values of the individual parameters are somewhat arbitrary, selected to provide a performance challenge to the anticipated range of skills of a target pool of testees. The use of other or alternative benchmark values and scoring formulas is within the scope of the invention. Also, the selection and ratio or weight giving to each performance parameter in the reduction process is somewhat arbitrary, the requirement being that each parameter is given a weight or degree of consideration recognized to be relevant to the overall performance.

The reduction process of primary performance parameters into a final kinetic index in the context of a golf swing analysis reflects the kinetic chain philosophy, that the performance value of the total motion is the sum of the performance value of the component parts of the motion executed in an optimal sequence, in order to transfer maximum energy and accuracy from feet to hips to shoulders to arms to the club and ultimately to the ball.

While this description of motion analysis and performance measurement has been cast in the context of a golf swing; the apparatus and methodology is equally applicable to other athletic motions involving, for example, running and kicking leg motions and swinging or chopping hand and arm motions.

Having evaluated individual performance parameters, which may also be referred to as "diagnostic" parameters, the system is able to compare the performance results to a catalog of exercises appropriate to the respective parameters and their test result, and provide an automated recommendation or prescription of exercises. The system may be further preprogrammed with the testee's available training schedule and hence able to tailor the prescription to the training time available, with emphasis on the parameters most in need of improvement. In other words, referring back to FIG. 1, the invention extends the automated, objective, Report on performance to include a Prescription for improvement.

In this regard, performance parameters are also characterized as diagnostic parameters. In the golf swing context, they may relate to subsets, body segments or components of the motion including: feet, hip; and shoulder performance. For example, diagnostic parameters of CBL (center balance line) extension and flexion, and of CAL (center alignment line) left and right lateral bending, relate to feet performance. Exercises appropriate to CBL extension problems are scaled according to a pre-determined scheme to the severity or priority of the problem, on a scale of 0 (acceptable performance) to −20 degrees (significantly below acceptable performance). A rating of −5 degrees may generate a prescribed exercise called "posture stick", using particular training tools; a relatively lower rating of −10 may call for the same exercise but with a different training tool; and so on. The "posture stick" exercise, for example, requires manipulation of a club in a prescribed manner while standing on a base platform, to acquire and practice attaining a stance with the correct alignment of the major joint centers of the body for creating an optimal muscle length tension relationship to enhance the body's postural equilibrium. Other exercises are similarly focused on particular body segments and components of the golf swing.

The initial selection of exercises and tools and the pre-determined scheme for allocation of particular exercises for improving particular performance parameters is somewhat arbitrary, but calculated to induce improvements in performance of components of motion and hence to the total motion performance if practiced as prescribed. The following table 1 lists one embodiment of diagnostic parameters and appropriate exercises by priority by which prescriptions would be issued by the system to a user.

TABLE 1

Diagnostic Parameters and Exercises Relating to Components of Motion

| Subject Area | Test/Measurement Parameter | Deviation (degrees) | Prescribed Exercise/Tool |
|---|---|---|---|
| Feet Posture #1 | Center Balance Line Extension | 0 | No Drill |
| | | −5 | Posture Stick/K-Pillow & club |
| | | −10 | Posture Stick/Full Foam Roller & club |
| | | −15 | Posture Stick/Half Foam Roller & club |
| | | −20 | Posture Stick/Base Platform & club |
| | Center Balance Line Flexion | 0 | No Drill |
| | | 5 | Posture Stick/K-Pillow & club |
| | | 10 | Posture Stick/Full Foam Roller & club |
| | | 15 | Posture Stick/Half Foam Roller & club |
| | | 20 | Posture Stick/Base Platform & club |
| Feet Posture #2 | Center Align. Line, Left Lat. Bend. | 0 | No Drill |
| | | −2 | Mini Drawbacks/Balance Board & club |
| | | −5 | Mini Swings/Balance Board & club |
| | | −10 | Mini Swings Level 2/Balance Bd & club |

TABLE 1-continued

Diagnostic Parameters and Exercises Relating to Components of Motion

| Subject Area | Test/Measurement Parameter | Deviation (degrees) | Prescribed Exercise/Tool |
|---|---|---|---|
| | | −15 | Mini Swings Level 1/Balance Bd & club |
| | | −20 | Mini Swings/Base Platform & 5 Iron |
| | Center Align. Line, Rt. Lat. Bend. | 0 | No Drill |
| | | 2 | Mini Drawbacks/Balance Board & club |
| | | 5 | Mini Swings/Balance Board & club |
| | | 10 | Mini Swings Level 2/Balance Bd & club |
| | | 15 | Mini Swings Level 1/Balance Bd & club |
| | | 20 | Mini Swings/Base Plaform & 5 iron |
| Hip | Rotation, Left | −20 | No Drill |
| | | −25 | Hockey Swings/Base Platform & club |
| | | −30 | Double Post Swing/Base Platform & club |
| | | −35 | Mini Swings/Full Foam Roller & club |
| | | −40 | Mini Swings/Half Foam Roller & club |
| | Rotation, Right | 20 | No Drill |
| | | 25 | Hockey Swings/Base Platform & club |
| | | 30 | Double Post Swing/Base Platform & club |
| | | 35 | Mini Swings/Full Foam Roller & club |
| | | 40 | Mini Swings/Half Foam Roller & club |
| Shoulders | Rotation, Left | (neg)0-10 | No drill |
| | | (neg)15-20 | Torso Twist/Base Platform & Stability Ball |
| | | (neg)25-30 | Torso Twist Counter & Primary/Base Plat. |
| | | (neg)35-40 | Torso Twist Blast/Base Platform |
| | | (neg)45-50 | Torso Twist Drawbacks/Base Platform |
| | Rotation, Right | 0-10 deg | No drill |
| | | 15-20 deg | Torso Twist/Base Platform & Stability Ball |
| | | 25-30 deg | Torso Twist Counter & Primary/Base Plat. |
| | | 35-40 deg | Torso Twist Blast/Base Platform |
| | | 45-50 deg | Torso Twist Drawbacks/Base Platform |
| Hip | Linear Address to Max Backswing | 0-2 cm | Double Post Swings/club |
| | | 3-5 cm | Bentley Swings/Base Platform & club |
| | | 6-8 cm | Hans Jumps/Impact Bag & Base Platform |
| | Linear Impact to Max Finish | 0-2 cm | Double Post Swings/club |
| | | 3-5 cm | Bentley Swings/Base Platform & club |
| | | 6-8 cm | Hans Jumps/Impact Bag & Base Platform |
| Hips | Static Posture | 0 | No drill |
| | | 1-10 deg | Posture Stick/Base Platform & club |
| Shoulders | Static Posture | 0 | No drill |
| | | 1-10 deg | Posture Stick/Base Platform & club |

Table 1: Diagnostic Parameters and Exercises Relating to Components of Motion

Explanations and detailed instructions for the user's prescribed exercises are available on the local system 70, or may be accessed directly or remotely via an internet access to a host enterprise (FIG. 2) with which the local system 70 is affiliated.

Referring to FIG. 1, steps of Test 100—Prescribe 500 require at least a local system 70, while the exercise step 600 is, of course, executed by the testee until he or she is ready to retest. A change in performance in a given primary parameter may or may not change the final kinetic index, but it will result in a change in prescription to a next level of exercise applicable to that performance parameter.

The description above is largely directed to exemplary embodiments of the invention. Specificity of language and statements of advantageous performance in this specification do not imply any commensurate limitation on the scope of the invention, nor do they require the stated performance. Thus no one embodiment disclosed herein is essential to the practice of another unless indicated as such. Indeed, the invention, as supported by the disclosure including specification, claims, abstract of the disclosure, and figures provided, includes all systems and methods that can be practiced from all suitable combinations of the various aspects disclosed, and all suitable combinations of the exemplary elements listed. Such combinations have particular advantages, including advantages not specifically recited herein.

Alterations and permutations of the proffered embodiments and methods will become apparent to those skilled in the art upon review of the specification, claims and drawings. Although the disclosed system is particularly suitable for analysis and improvement of golf swings, variations can be implemented, for example, for analysis and improvement of other athletic motions such as racquet sport swings like tennis, or for analysis of other motions, including animal motions, particularly using the biofeedback mode and motion analysis and prescription techniques, such as to diagnose and recommend courses of treatment for physical therapy. Accordingly, none of the disclosure of the embodiments and methods constrains the scope of the invention. Rather, the claims issuing hereon or on one or more applications claiming benefit of this application or the applications to which it claims priority will variously define the invention.

A system and method for analyzing and improving the performance of an athletic motion such as a golf swing may require: instrumenting a user with inertial sensors and optionally with video cameras and monitoring a golf swing or other athletic motion of interest; drawing upon and contributing to a vast library of performance data for analysis of the test results; the analysis including scoring pre-defined parameters relating to component parts of the motion and combining the parameter scores to yield a single, kinetic index score for the motion; providing an information rich, graphic display of the results in multiple formats including video, color coded and stepped frame animations from motion data, and synchronized data/time graphs; and based on the results prescribing a user-specific training regime with exercises selected from a library of standardized exercises using standardized tools and training aids.

Other and various examples and embodiments equivalent to and within the scope of the claims that follow will be apparent to those skilled in the art.

We claim:

1. A method for analysis of a body motion of an animal or human subject, comprising:

using a computer-based motion analysis system comprising multiple, body mountable, inertial sensors in communication with a processing computer connected to a computer-driven display screen;

mounting the multiple inertial sensors to the body of an animal or human subject of interest at target areas of the body relating to a body motion of interest;

calibrating the inertial sensors for initial alignment and orientation of each respective target area of the body;

setting range of motion limits for selected body segments of said body motion;

monitoring the execution of a said body motion with the motion analysis system;

collecting sensor data from said motion sensors;

processing said sensor data so as to generate an animation and motion data representing the body motion of said subject, said animation comprising at least two color coded body segments wherein one body segment is color coded in a different color than the other body segment;

displaying the animation of the body motion on the display screen;

displaying on the display screen a visually apparent, rectangular, three dimensional open frame cage representing said motion limits for each said selected body segment, within which said animation of said selected body segment is visible; and comparing the generated motion data to existing motion data and calculating performance parameters related to the body motion.

2. The method of claim 1, comprising:
prescribing a regime of training exercises selected from a pre-defined list of exercises where each exercise is associated with at least one said performance parameter, and the order and amount of each exercise of the prescribed regime is associated with the relative levels of said performance parameters.

3. The method of claim 1, said body motion requiring manipulation of an associated object, said subject comprising the individual and the associated object in combination.

4. The method of claim 1, further comprising:
altering a selected color on the display screen upon the occurrence of a body motion exceeding said motion limits.

5. The method of claim 1, said mounting the multiple inertial sensors to the body comprising attaching said sensors to at least one body appliance worn by the subject, the sensors and said at least one appliance having corresponding mating structure by which a said sensor may be uniformly and repeatably attached with the same orientation to the appliance.

6. The method of claim 1, said existing motion data being user-selectable from a database of existing motion data.

7. The method of claim 1, said sensor data comprising linear motion, linear velocity, rotational motion, and rotational velocity, in three dimensions, for each said sensor.

8. The method of claim 1, further comprising:
communicating motion related instructions to the subject; said computer-based motion analysis system comprising means for communicating said motion related instructions to the subject.

9. The method of claim 8, further comprising:
communicating motion related performance reports to the subject; said computer-based motion analysis system comprising means for communicating motion related performance reports to said subject.

10. The method of claim 2, said computer-based motion analysis system comprising means for communicating said regime of training exercises to the subject.

11. The method of claim 1, comprising
displaying said motion data on the display screen.

12. The method of claim 11, said motion data comprising a time-based graph of selected said performance parameters.

13. The method of claim 1, comprising:
setting range of motion limits for selected body segments of said body motion in advance of said monitoring; and
generating a first audio feedback signal upon the occurrence of said body motion conducted within said range of motion limits, and a different audio feedback signal upon the occurrence of a said body motion exceeding said range of motion limits.

14. The method of claim 1, said inertial sensors incorporating wireless data transmitters, said computer-based motion analysis system incorporating a wireless data receiver.

15. The method of claim 1, said computer-based motion analysis system comprising a video camera connected to the system; said method comprising:
monitoring the execution of a said body motion with the camera;
collecting a video signal of the body motion;
displaying the video signal on the display screen concurrently with said animation and said motion data.

16. A method for analysis of a body motion of an animal or human subject, comprising:
using a computer-based motion analysis system comprising multiple, body mountable, inertial sensors in communication with a processing computer connected to a computer-driven display screen, at least one wearable body appliance configured to accept the attachment of said sensors thereto, and means for communicating motion related instructions and performance parameters to a system operator;
attaching the inertial sensors to a selected animal or human subject using the at least one wearable body appliance such that the sensors are located at target areas of the body relating to a body motion of interest;
calibrating the inertial sensors for initial alignment and orientation of each respective target area of the body;
setting range of motion limits for selected body segments for said body motion;
communicating said motion related instructions to the system operator;
monitoring the execution of a said body motion with the motion analysis system;
collecting sensor data from said motion sensors;
processing said sensor data so as to generate animation and motion data representing said body motion, said animation comprising at least two color coded body segments wherein one body segment is color coded in a different color than the other body segment;
displaying the animation and motion data of the body motion on the display screen;
displaying on the display screen a visually apparent, rectangular, three dimensional open frame cage representing said motion limits for each said selected body segment, within which said animation of said selected body segment is visible;
comparing the generated motion data to said motion limits and signaling the system operator when said limits are exceeded;
comparing the generated motion data to existing motion data selected from a computer database of exiting motion data, and calculating said performance parameters there from;
communicating said performance parameters to the system operator.

17. The method of claim 16, comprising:
prescribing a regime of training exercises selected from a pre-defined list of exercises where each exercise is associated with at least one said performance parameter, and the order and amount of each exercise of the prescribed regime is associated with the relative levels of said performance parameters; and
communicating the regime of training exercises to the system operator.

18. The method of claim 16, comprising:
associating the generated said motion data with the subject and the date of collection and saving it to the computer database of existing motion data.

\* \* \* \* \*